(12) United States Patent
Gokaraju et al.

(10) Patent No.: US 11,122,829 B2
(45) Date of Patent: Sep. 21, 2021

(54) DIETARY SUPPLEMENTS AND COMPOSITIONS FOR ENHANCING PHYSICAL PERFORMANCE AND ENERGY LEVELS

(71) Applicant: LAILA IMPEX, Vijayawada (IN)

(72) Inventors: Ganga Raju Gokaraju, Vijaywada (IN); Trimurtulu Golakoti, Vijayawada (IN); Rama Raju Gokaraju, Vijayawada (IN); Kiran Bhupathiraju, Vijayawada (IN); Venkata Kanaka Ranga Raju Gokaraju, Vijayawada (IN); Krishanu Sengupta, Vijayawada (IN); Venkata Krishna Raju Alluri, Vijayawada (IN)

(73) Assignee: Laila Impex, Vijayawada (IN)

( * ) Notice: Subject to any disclaimer, the term of this patent is extended or adjusted under 35 U.S.C. 154(b) by 41 days.

(21) Appl. No.: 16/196,896

(22) Filed: Nov. 20, 2018

(65) Prior Publication Data

US 2019/0191752 A1    Jun. 27, 2019

Related U.S. Application Data

(63) Continuation-in-part of application No. PCT/IN2017/050191, filed on May 20, 2017.

(51) Int. Cl.

| | | |
|---|---|---|
| *A61K 36/00* | (2006.01) | |
| *A23L 33/105* | (2016.01) | |
| *A61K 36/482* | (2006.01) | |
| *A61K 36/22* | (2006.01) | |
| *A61K 36/185* | (2006.01) | |
| *A61K 36/48* | (2006.01) | |
| *A23L 2/52* | (2006.01) | |
| *A61P 21/00* | (2006.01) | |
| *A61K 36/28* | (2006.01) | |
| *A61K 36/74* | (2006.01) | |

(52) U.S. Cl.
CPC ............. *A23L 33/105* (2016.08); *A23L 2/52* (2013.01); *A61K 36/185* (2013.01); *A61K 36/22* (2013.01); *A61K 36/28* (2013.01); *A61K 36/48* (2013.01); *A61K 36/482* (2013.01); *A61K 36/74* (2013.01); *A61P 21/00* (2018.01); *A23V 2002/00* (2013.01); *A23V 2200/316* (2013.01); *A23V 2200/322* (2013.01); *A23V 2250/21* (2013.01)

(58) Field of Classification Search
None
See application file for complete search history.

(56) References Cited

U.S. PATENT DOCUMENTS

| | | | | |
|---|---|---|---|---|
| 2008/0254157 A1* | 10/2008 | Chauhan | ................ | A61K 36/28 424/777 |
| 2014/0030332 A1* | 1/2014 | Baron | .................... | A61K 9/209 424/474 |
| 2015/0352172 A1* | 12/2015 | Gokaraju | ............... | A61K 36/38 424/739 |

FOREIGN PATENT DOCUMENTS

| | | | | |
|---|---|---|---|---|
| WO | WO-2010100653 A2 * | 9/2010 | ............. | A61K 35/12 |
| WO | 2012/140666 A2 | 10/2012 | | |
| WO | WO-2012140666 A3 * | 1/2013 | | |

OTHER PUBLICATIONS

Dubey et al. (2000) Asian Journal of Chemistry, vol. 12, No. 2: 577-578. (Year: 2000).*

(Continued)

*Primary Examiner* — Russell G Fiebig
(74) *Attorney, Agent, or Firm* — Kramer Amado

(57) ABSTRACT

The invention discloses novel dietary supplements or herbal product comprising at least one ingredient selected from the extracts or fractions derived from *Bauhinia racemosa* fruit, *Cassia auriculata*, *Mangifera indica* stem bark, *Woodfordia fruticosa* tender stem and *Acacia nilotica* fruit or their compositions in combination with at least one compound selected from biological actives, herbal extracts, minerals, amino acids, proteins, vitamins, excipient, diluent or carrier as a natural energy enhancer to provide an onset and steady maintenance of energy and for improving muscle strength, muscle mass and mental alertness, for treating sarcopenia and muscular atrophy in a warm blooded animal or mammal in need thereof.

20 Claims, 4 Drawing Sheets

(56) References Cited

OTHER PUBLICATIONS

Ghouse et al. (2000) J. Innovations Pharm. Biol. Sci. vol. 2, Issue 1: pp. 96-105. (Year: 2000).*
Khurana et al. (2016) Pharm Pat. Anal. 5(3): 169-181. (Year: 2016).*
Rymbai et al. (2013) Journal of Horticultural Science and Biotech. 88(4): 369-379. (Year: 2013).*
Arya et al. (2015) J. Ethnopharmacology 175: 229-240. (Year: 2015).*
Basha et al. (2011) Drug Invention Today 3(7): 165-168. (Year: 2011).*
Bhutkar et al. (2018) National J. Basic Med. Sci. vol. 8, Issue 3, pp. 160-166. (Year: 2018).*
Kumar et al. (2017) Clinical Phytoscience, 3:7 (9 pages). (Year: 2017).*
Ngo et al. (2019) Sci. Pharm. 87 (12 pages). (Year: 2019).*
Patatakijanavich et al. (2019) Sonklanakarin J. Sci. Technol. 41(4): 943-951. (Year: 2019).*
Ramachandran et al. (2011) Evidence-based Complementary and Alternative Medicine, vol. 2011, Article 571721 (8 pages). (Year: 2011).*
Ramachandran (2013) Pharmacogn. Rev. 7(14): 157-169. (Year: 2013).*
Galani et al. (2010) Int. J. Ayurveda Res. 1(4): 247-253. (Year: 2010).*
Stern et al. (2013) J. Med. Food 16(6): 529-537. (Year: 2013).*
International Search Report dated Oct. 5, 2017 in connection with PCT/IN2017/050191.
Written Opinion of the International Searching Authority dated Oct. 5, 2017 in connection with PCT/IN2017/050191.

* cited by examiner

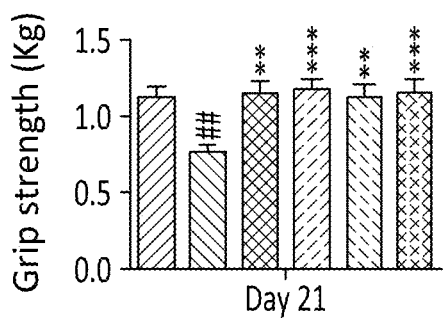
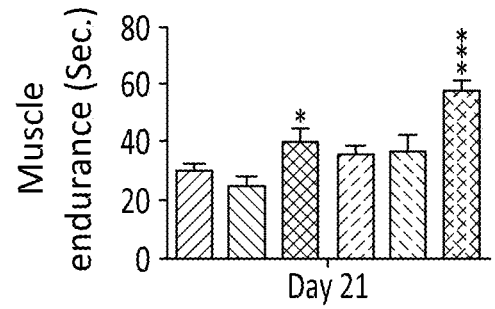
FIG. 4A                                   FIG. 4B
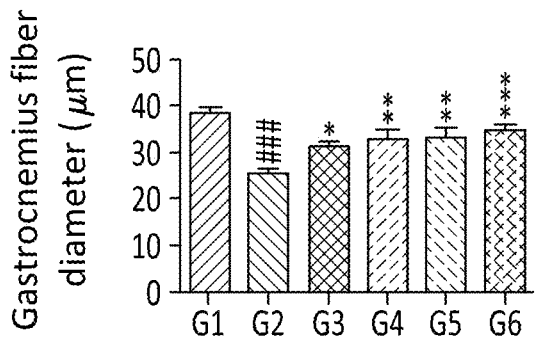
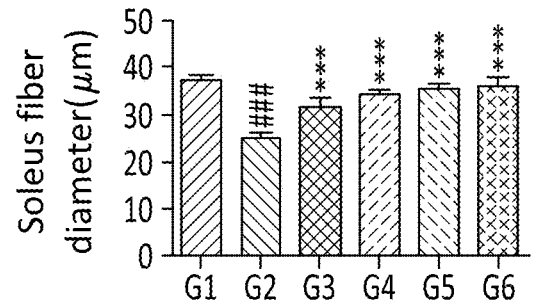
FIG. 4C                                   FIG. 4D
Values are represented as mean + S.E.M.; n=6 animals per group. ###P<0.001, ##P<0.01 as compared to Vehicle control (G1), *P<0.001 P<0.01 and *P<0.05 as compared to disease control (G2) group using two-way ANOVA followed by bonferroni post-test.

DIETARY SUPPLEMENTS AND COMPOSITIONS FOR ENHANCING PHYSICAL PERFORMANCE AND ENERGY LEVELS

CROSS-REFERENCE TO RELATED APPLICATIONS

This application is a continuation-in-part of International Patent Application No. PCT/IN2017/050191, filed May 20, 2017, published as WO 2017/203540; which claims priority to Indian Patent Application 201641013908, filed May 21, 201. The entire disclosure of each prior application is hereby incorporated by reference in its entirety.

TECHNICAL FIELD OF THE INVENTION

The present invention relates to novel dietary herbal supplements selected from the extracts and fractions derived from *Bauhinia racemosa, Mangifera indica, Woodfordia fruticosa, Cassia auriculata* and *Acacia nilotica* either alone and their compositions as natural energy enhancer for enhancing physical performance, muscle mass, muscle strength, energy levels and for treating Sarcopenia and muscular atrophy in a mammal.

The present invention further relates to food ingredient formulations such as beverages, dietary ingredient formulation, snacks and energy drinks containing the said herbal ingredient or its compositions for onset and steady maintenance of energy, muscle strength and mental alertness and for enhancing muscle power, physical activity, physical fitness, mental alertness, energy levels, stamina levels, circulatory health, blood vessel health or for better physical and mental health.

BACKGROUND OF THE INVENTION

The common description of energy is the ability of a system to perform work. All activities of human life require the presence of energy. Energy is needed to sustain life and every aspect of existence such as thinking, feeling, walking, eating, drinking, dreaming, breathing etc. Energy is felt and experienced upon its expenditure from body's energy reserves, not through its accumulation. Age, fatigue and stress make people feel deficient in energy. This drag in energy very often compromises body's mental alertness. The efficiency at work place and personal management can be enhanced by addressing body's energy demands properly. In addition to energy, muscular strength and muscular endurance are important factors to improve the physical agility of a person. Muscle strength is a measure of how much force a person's muscles can exert, while endurance is the measure of how many times the muscles can repeat a specific exertion of force.

Sarcopenia is the loss of skeletal muscle mass and strength associated with ageing process (Cruz-Jentoft et al 2010; Fielding et al 2011). It affects balance, gait and overall ability to perform daily routine tasks. The causes of Sarcopenia are multifactorial which includes sedentary lifestyle, altered endocrine functions, chronic diseases, inflammation, insulin resistance and nutritional deficiencies. The therapeutic options for Sarcopenia are unclear and constantly evolving. The most rational approach to delay the progression and treatment of Sarcopenia is based on the combination of proper nutrition, associated with the use of dietary supplements, and a regular exercise program.

Dietary supplements are used to increase their physical performance, physical fitness, improve their health, or reduce the potentially negative consequences of physical activity such as injury and chronic fatigue, or suppressed immune function.

Many energy beverages, supplements and food ingredient formulations containing proteins, amino acids and vitamins along with numerous other agents are presently available in the market, but they are highly rich in carbohydrate complexes. As such these formulations act too quickly to give instant energy, but do not sustain the levels over period of time. Many of these formulations tend to increase the blood glucose levels sharply and this is followed by their rapid depletion, which might sometimes lead to complications.

The disadvantages apart from high sugar content include high caffeine content, alcohol content and use of other ingredients such as amino acids, taurine, guarana and ginseng, in such small amounts with no beneficial health effects. Further disadvantages of energy drinks are that it comes with daily recommended limits, to limit the daily consumption.

In the light of the foregoing, there remains a need in the art to provide natural supplements, which improve the feeling of being energetic, general agility, endurance and mental alertness without having any health complications.

Therefore, the present invention addresses the existing need in the art by providing extracts and compositions to enhance energy, endurance, muscle strength, muscular endurance and/or mental alertness. Thus, the present invention provides natural extracts, fractions and/or composition(s) capable of increasing energy levels for an extended period of time in a mammal to enhance energy levels, muscle power, muscular endurance and mental alertness and thus solves these needs.

*Bauhinia racemosa*, belongs to the family Caesal piniaceae. In Traditional Ayurveda the bark of *Bauhinia racemosa* is used in the treatment of malaria, dysentery and diarrhea, asthma, and skin conditions like rashes, pimples, Acne, abscess and ulcers and the leaves are used as a cattle fodder.

*Mangifera indica*, commonly known as mango belongs to the genus *Mangifera* of the family Anacardiaceae. It has been used in the Ayurveda over 4000 years and is the national fruit of India, Pakistan and the Philippines. Most parts of the mango tree are useful to treat various medical conditions such as heat stroke, wound healing, degenerative disease, diabetes, diarrhea, dysentery, anemia, asthma, bronchitis, cough, hypertension, insomnia, rheumatism, toothache, leucorrhoea, hemorrhage and piles etc. Fruit is edible. Bark, leaves, stem, tender stems and seed are widely used for their medicinal potential.

*Woodfordia fruticosa* commonly known as Dhataki and is found in Sri Lanka, South Konkan and north India. *Woodfordia fruticosa* belongs to the family Lythraceae. It is used as a fermenting agent for the preparation of Asava and Arishta in ayurveda. It is also known to treat Bowel problems, haemorrhages, menorrhagia and seminal weakness, fever, headache, herpes.

*Acacia nilotica* belongs to the genus *Acacia* of the family Leguminosae/Fabaceae-Mimosodeae. It was widely used in the Egyptian Traditional medicines to treat various medical conditions which include stomach upset and pain, scurvy, as an anti-septic, expectorant, tuberculosis, leprosy, smallpox, dysentery, cough, ophthalmia, toothache, skin cancer, as astringent, antispasmodic, and aphrodisiac. Leaves, bark, fruit and seed are commonly used for their health benefits.

SUMMARY OF THE INVENTION

The present invention provides novel herbal extracts and fractions derived from *Acacia nilotica, Bauhinia racemosa,*

*Cassia auriculata, Mangifera indica* and *Woodfordia fruticosa* for increasing energy levels, increasing endurance for an extended period of time, improve muscle development, muscle power mental alertness and treating Sarcopenia and muscular atrophy.

The present invention provides novel herbal extracts and their dietary supplement compositions comprising at least two ingredients/components selected from the extracts or fractions derived from *Acacia nilotica, Bauhinia racemosa, Cassia auriculata, Mangifera indica* and *Woodfordia fruticosa*, which are capable of increasing energy levels for an extended period of time, improve muscle development and power and mental alertness.

In yet another aspect, the invention provides novel dietary supplement compositions comprising at least one ingredient selected from the extracts and fractions derived from *Acacia nilotica, Bauhinia racemosa, Cassia auriculata, Mangifera indica* and *Woodfordia fruticosa*, in combination with at least one ingredient selected from active compound(s), extracts, phytochemical(s), derived from plant(s), animal(s) or microorganisms with proven therapeutic health benefits; pharmaceutically or dietetically acceptable diluents, excipients and carriers; vitamins, amino acids and minerals, useful for increasing energy levels, endurance for an extended period of time, improving muscle development, muscle power, mental alertness and for treating Sarcopenia and muscular atrophy.

In another aspect, the invention provides dietary supplements, food ingredient formulations such as beverages, snacks and energy drinks containing the above said ingredient(s) or its composition(s) for the onset and steady maintenance of energy and mental alertness. The formulation is useful for enhancing muscle power, physical activity, physical fitness, mental alertness, muscle mass, energy levels, stamina levels, circulatory health, blood vessel health or for better physical & mental health and treating Sarcopenia and muscular atrophy in a mammal.

In yet another aspect, the invention provides novel extracts or fractions derived from *Acacia nilotica, Bauhinia racemosa, Cassia auriculata, Mangifera indica*, and *Woodfordia fruticosa*, and their compositions for the onset and steady maintenance of energy; muscle strength, mental alertness and for enhancing muscle power, muscle mass, physical activity, physical fitness, mental alertness, energy levels, stamina levels, circulatory health, blood vessel health or for better mental health in warm blooded animals in need thereof.

In yet another aspect, the invention provides a method of increasing energy, muscle mass and endurance to provide an onset and steady maintenance of energy, muscle strength, muscle endurance and mental alertness; and for treating sarcopenia and muscular atrophy in a mammal, wherein the method comprises supplementing or treating the said mammal with at least one ingredient selected from the extracts or fractions derived from *Acacia nilotica, Bauhinia racemosa, Cassia auriculata, Mangifera indica*, and *Woodfordia fruticosa*, and their compositions.

Various embodiments disclosed herein relate to a synergistic mixture of at least two ingredients selected from the group consisting of an extract of *Acacia nilotica*, an extract of *Bauhinia racemosa*, an extract of *Cassia auriculata*, an extract of *Mangifera indica*, an extract of *Woodfordia fruticosa*, an extract of *Sphaeranthus indicus*, an extract of *Punica granatum* fruit rind, an extract of *Rubia cordifolia*, and a mixture thereof. The synergistic mixture may be used in combination with at least one compound selected from the group consisting of excipients, diluents, and carriers. In a binary composition, the amount of each extract is between 10% and 90% of the synergistic mixture; between 20% and 80% of the synergistic mixture; between 30% and 70% of the synergistic mixture; or between 40% and 60% of the synergistic mixture. Where more than two extracts are used in combination, the amount of each extract is between 5% and 90% of the synergistic mixture; between 5% and 65% of the synergistic mixture; between 5% and 50% of the synergistic mixture; between 10% and 80% of the synergistic mixture; between 20% and 60% of the synergistic mixture; between 10% and 30% of the synergistic mixture; or between 10% and 15% of the synergistic mixture.

Various embodiments disclosed herein relate to a synergistic mixture of at least one first ingredient selected from the group consisting of an extract of *Acacia nilotica*, an extract of *Bauhinia racemosa*, an extract of *Cassia auriculata*, an extract of *Mangifera indica*, an extract of *Woodfordia fruticosa*, and a mixture thereof; and at least one second ingredient selected from the group consisting of an extract of *Sphaeranthus indicus*, an extract of *Punica granatum*, an extract of *Rubia cordifolia*, and a mixture thereof. The first and second ingredients may be used in a ratio of between 4:1 and 1:4, between 3:1 and 1:3, between 2:1 and 1:2, between 1.5:1 and 1:1.5, or about 1:1.

Various embodiments disclosed herein relate to an herbal composition comprising a first mixture containing an extract of *Mangifera indica* and a second component in a ratio by weight of from 4:1 to 1:4, from 3:1 to 1:3, from 2:1 to 1:3, from 2:1 to 1:2, or about 1:1, said second component being an extract of a plant selected from the group consisting of *Acacia nilotica, Cassia auriculata, Sphaeranthus indicus*, and mixtures thereof. Various embodiments disclosed herein relate to an herbal composition comprising a second mixture comprising an extract of *Cassia auriculata* and a fourth component in a ratio of from 4:1 to 1:4, from 3:1 to 1:3, from 2:1 to 1:3, from 3:1 to 1:2, from 2:1 to 1:2, or about 1:1, said fourth component being an extract of a plant selected from the group consisting of *Acacia nilotica, Punica granatum, Rubia cordifolia*, and mixtures thereof. Various embodiments disclosed herein relate to an herbal composition comprising a combination of the first and second mixtures. The herbal composition may comprise:

the first mixture, the second mixture, or a combination thereof, and an extract of *Bauhinia racemosa, Woodfordia fruticose*, or a mixture thereof.

In various embodiments, the herbal composition comprises an extract of *Mangifera indica* and a second component in a ratio of between 2:1 and 1:3, the second component comprising an extract of at least one of *Acacia nilotica, Cassia auriculata*, and *Sphaeranthus indicus*.

In various embodiments, the herbal composition comprises an extract of *Cassia auriculata* and a fourth component in a ratio of between 3:1 and 1:3, the fourth component being an extract of a plant selected from the group consisting of *Acacia nilotica, Punica granatum, Rubia cordifolia*, and mixtures thereof.

DESCRIPTION OF THE FIGURES

FIG. 2A), *Woodfordia fruticosa* tender stem (LN16008; FIG. 2B), *Acacia nilotica* fruit (LN16011; FIG. 2C), alcohol extract of *Cassia auriculata* leaves (LN17090; FIG. 2D) and composition-3 (FIG. 2E). FIG. 2F is a bar diagram representing the inhibition of 20S proteasome by extract LN17090 and composition-3.

FIGS. 4A to 4D: Bar diagrams representing improvement of grip strength (FIG. 4A), Muscular endurance (FIG. 4B), gastrocnemius muscle fiber diameter (FIG. 4C) and soleus muscle fiber diameter (FIG. 4D) in Sarcopenia model of SD rats for the treatment groups supplemented with 200 mg of LN17090 (G3), 400 mg of LN17090 (G4), 200 mg of LN16011 (G5) and 350 mg of HMB (G6) in comparison with vehicle control (G1) and disease control (G2) groups.

DETAILED DESCRIPTION OF THE INVENTION

Figure 1A:
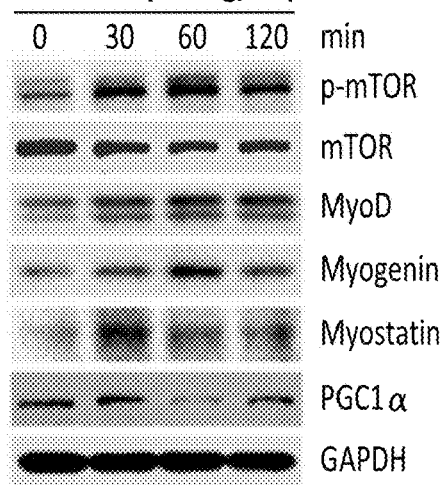
FIGS. 1A to 1F: Representative immunoblot images depict LN16002 (FIG. 1A), LN16008 (FIG. 1B), LN16011 (FIG. 1C), LN17090 (FIG. 1D), Composition 3 (FIGS. 1E and 1F) hyper-phosphorylate mTOR protein and increases production of muscle specific transcription factors such as mTOR, PGC 1 α, myostatin, MyoD and Myogenin in L6 rat skeletal myoblasts. Expression of GAPDH protein represents the loading control.

The invention will now be described in detail in connection with certain preferred and optional embodiments, so that various aspects thereof may be more fully understood and appreciated. However, any skilled person will appreciate the extent to which such embodiments could be extrapolated in practice.

Source of the Plant Materials:

The plants used in the present invention viz., *Acacia nilotica*, *Bauhinia racemosa*, *Mangifera indica*, and *Woodfordia fruticosa* were collected in India. The extracts derived from *Acacia nilotica* dried fruit; *Bauhinia racemosa* dried fruit, *Cassia auriculata* aerial parts, *Mangifera indica* stem bark, *Woodfordia fruticosa* tender stem plant part raw material and a few other plant parts of these plants were used to demonstrate the invention. Other plant parts and extract fractions can also be used in the similar manner.

Rationale of Performing NO Assay, ATP Assay and Other Assays

The presence and sustenance of energy is the basic requirement and condition behind all activities of human life. Adequate supply of nutrients and oxygen through enhanced blood circulation to working muscles is thus essential, especially during physical activity and exercise. Nitric oxide (NO) produced by vascular endothelial cells is known as a potent vasodilator, which makes blood vessels to expand, thus providing more supply of oxygen and nutrients to the muscle cells during workouts. Hence, the plant extracts and compounds with NO enhancing property can help in prolonging the endurance during exercise and physical activities. As NO has short life span nitrite levels were evaluated in the current studies.

Adenosine Triphosphate or ATP is the second most important complex molecule in the human body after DNA. ATP is responsible for supplying chemical energy for numerous cellular functions including cellular transport, production of biological molecules and functioning of macromolecules, which are essential for the existence and survival of the cell.

It supplies energy to heart muscle (for blood circulation) and skeletal muscle (for muscle contractions needed for gross body movement). For the first 5 or 6 seconds of intense physical action, such as running, muscular activity is dependent on the pool of ATP that is already present in the muscle cells. Beyond this time, new ATP is produced mostly through anaerobic process (glycolysis) and aerobic metabolism (cellular respiration through glycolysis, the citric acid cycle, and electron transport/oxidative phosphorylation). Overall, ATP enables the activation of muscular contractions that are needed to support longer and more vigorous physical activities. Therefore, it is essential to increase the intracellular energy source or ATP content during endurance exercise or for longer and intense period of physical activities.

Protein is the primary building block of muscles, bones and cartilage; and is essential for muscle growth and repair. Proteins are synthesized in the cells through translation process of mRNA utilizing amino acids. Therefore, stimulation of muscle protein synthesis is an important factor for increasing muscle mass. mTOR (mammalian target of rapamycin), a serine/threonine-protein kinase, is a central regulator of protein synthesis. Activated mTOR upregulates protein synthesis by phosphorylating key regulators of mRNA translation and ribosome synthesis. In addition, mTOR activation increases the production of muscle specific transcription factors like MyoD and Myogenin. Hence, plant extracts or dietary supplements, which activate mTOR signaling can have the potential to enhance the muscle development and endurance.

The mitochondria are site of oxidative energy production in cells and provide the majority of the total ATP required to maintain normal cellular function and homeostasis. ATP also plays a key role in skeletal muscle function as force generator for locomotion. Mitochondrial biogenesis is the process by which new mitochondria are formed in the cell through proliferation of pre-existing mitochondria. Mitochondrial biogenesis is accompanied not only by increase in number, but also in size and mass. Mitochondrial biogenesis is influenced by many environmental stresses including exercise and other physical activities. PGC-1α [PPAR (peroxisome proliferator-activated receptor)-γ coactivator-1α] is a major regulator of mitochondrial biogenesis.

In addition, Cytochrome C oxidase 1 (COX1) is a key subunit of the Cytochrome c Oxidase Enzyme (Complex IV), a mitochondrial protein located in the inner mitochondrial membrane and a key enzyme in the electron transport chain. The expression/activity of this respiratory enzyme is a straightforward approach for investigating mitochondrial health or mitochondrial biogenesis. The ratio of the level of Complex IV, or cytochrome c oxidase (COX-1) to Complex II, or succinate dehydrogenase (SDH-A) will determine the health and number of active mitochondria present in the cell. Increase in the COX-1/SDH-A ratio thus indicates that the mitochondria are healthy, and it is also an indirect measure of mitochondrial biogenesis.

Hence, the plant extracts that can induce mitochondrial biogenesis (proliferation, size and mass) through activation of PGC-1α and COX1 can have the potential to enhance the energy, endurance and muscle building.

Skeletal muscle's primary function is to support both voluntary and involuntary body movements. Hence a decent muscle mass is important factor for sustained physical activity or exercise. New muscle tissue is generated from myoblasts through a process called Myogenesis. Myoblasts are a type of embryonic progenitor cells that proliferate and differentiate through a process of fusion to form multinucleated fibers called myotubes. This differentiation process is regulated by myogenic regulatory factors, which include MyoD and myogenin. Myogenin is a muscle-specific transcription factor involved in the coordination of skeletal muscle development or myogenesis and repair. Myogenin is required for the fusion of myogenic precursor cells to either new or previously existing fibers during the process of differentiation. MyoD is other important regulatory protein factor that plays a major role in regulating muscle differentiation and muscle development. Myogenesis activation is good for muscle development and endurance.

Based on the above information, we hypothesized that the herbal extracts, fractions or their compositions/formulations which can enhance nitric oxide synthesis in endothelial cells; increase ATP content; activate protein synthesis/mTOR signaling, mitochondrial biogenesis, and myogenesis (myotube formation); and activate MyoD and myogenin signaling in skeletal muscle cells would be ideally promising for increasing energy and endurance level, and muscle tissue mass in physical performers such as body builders, athletes etc. Therefore, a thorough screening was conducted on the herbal extracts, fraction and their compositions in cell based studies to assess their ability to increase the synthesis of nitrite in endothelial cells and intracellular ATP and protein in skeletal muscle cells.

Figure 1B:
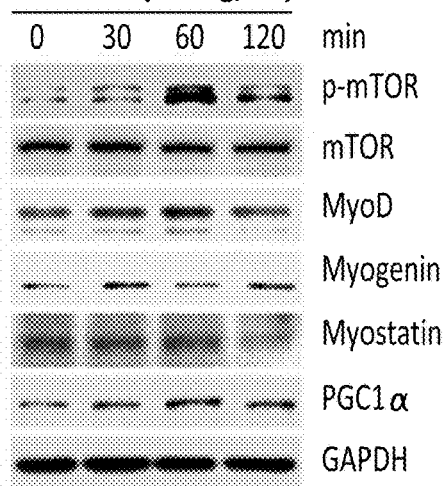
Figure 1C:
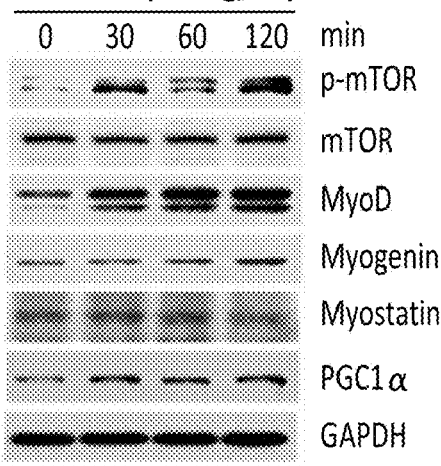
Figure 1D:
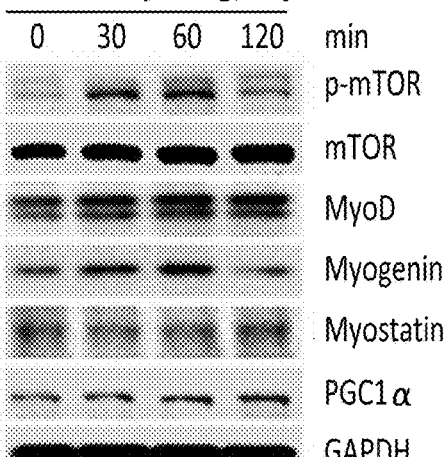
Figure 1E:
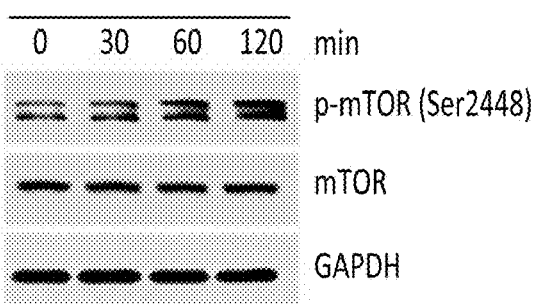
Figure 1F:
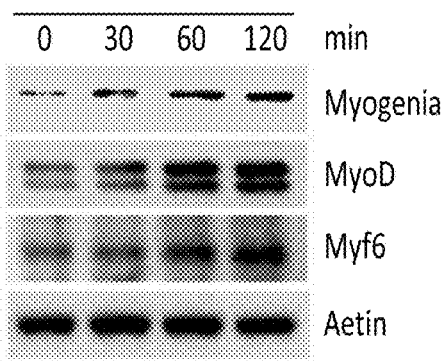
Figure 2A:
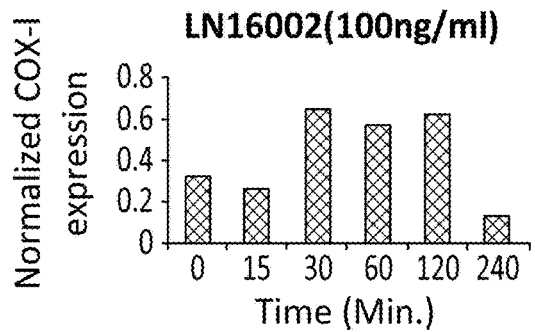
FIGS. 2A to 2F: Representative bar diagrams depict the modulation of Cytochrome C oxidase 1 (COX1) by extracts of *Bauhinia racemosa* fruit (LN16002.
Figure 2B:
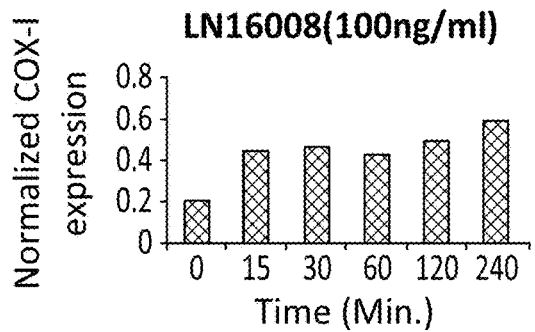
Figure 2C:
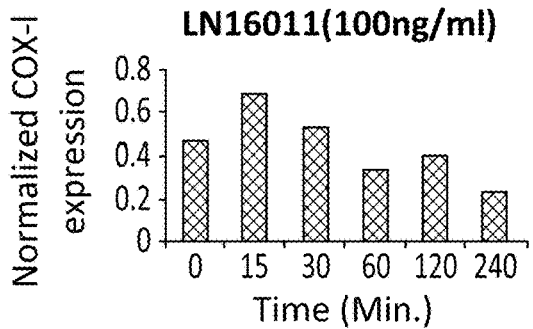
Figure 2D:
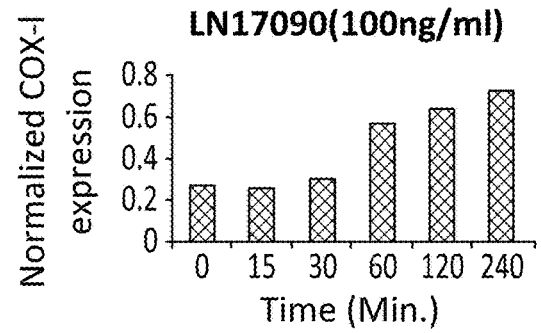
Figure 2E:
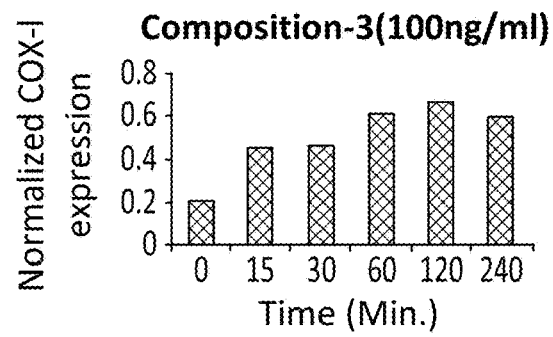
Figure 2F:
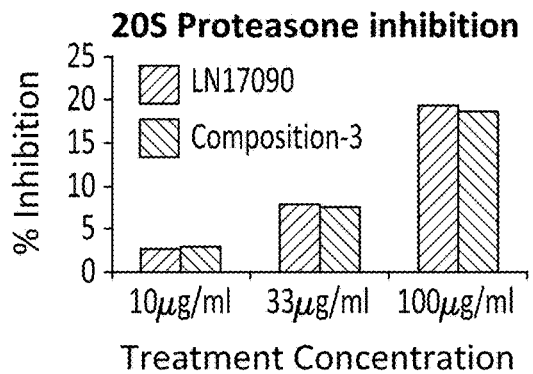

During the current screening study, it was found surprisingly that the hydroalcohol extracts derived from *Mangifera indica* bark (LN16005), *Woodfordia fruticosa* tender stem (LN16008) and *Acacia nilotica* fruit (LN16011), and alcohol extract derived from *Cassia auriculata* aerial parts (LI17090) potently increased nitrite production in EA.hy926 human endothelial cells as summarized in table 1. These extracts also increased the ATP production in rat L6 skeletal muscle cells as summarized in Table 5. The nitric oxide and ATP data obtained for extracts derived from other plant parts and those derived using other solvent media for extraction are also summarized in table-1 and 5 respectively. *Bauhinia racemosa* hydroalcohol extract (LN16002) and some other solvent extracts of the above herbs also increased ATP levels. Similarly, the L6 rat muscle skeletal myoblasts exposed to the above test compounds increased the expression of PGC-1α ([PPAR (peroxisome proliferator-activated receptor)-γ coactivator-1α] as depicted in FIGS. 1A to 1F, suggesting that these compounds can upregulate the mitochondrial biogenesis. The above compounds also showed efficacy in activating complex IV of mitochondrial electron transportation chain (ETC), as indicated by the overexpressing of Cyt. C Oxidase 1 (COX1) in L6 rat muscle skeletal myoblasts as depicted in FIGS. 2A to 2F. The over expressing master regulator PGC1α and activating complex IV are known to contribute to increased mitochondrial biogenesis. In tune with these observations, the extracts of *Bauhinia racemosa* fruit (LN16002), *Cassia auriculata* aerial parts (LI17090), *Mangifera indica* bark (LN16005), *Woodfordia fruticosa* tender stem (LN16008) and *Acacia nilotica* fruit (LN16011) exhibited increased Mitochondrial biogenesis in rat skeletal myoblasts. The data for PGC1α expression is depicted in FIGS. 1A to 1F. The data for activation of COX1 is depicted in FIGS. 2A to 2F. The data for mitochondrial biogenesis is summarized in table 12. Overall all, it is observed that the extracts can provide additional cellular energy source for enhanced energy and endurance, and also increase muscle mass, muscle strength, protection from aging, Sarcopenia and muscular atrophy.

Figure 3A:
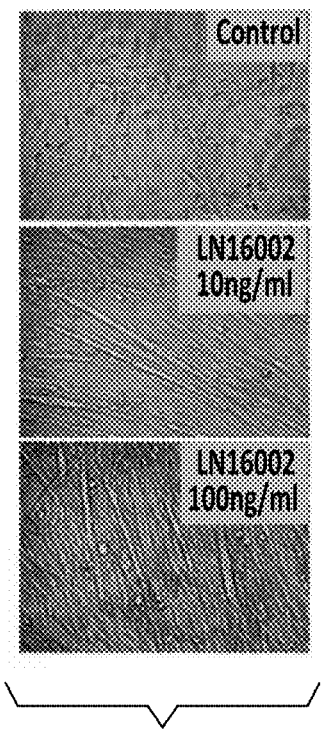
FIGS. 3A to 3E: Phase contrast images represent myotube formation in L6 rat myoblast cells induced by LN16002 (FIG. 3A), LN16008 (FIG. 3B), LN16011 (FIG. 3C), LN17090 (FIG. 3D) and Composition-3 (FIG. 3E) at different treatment concentrations as indicated. Vehicle control treated cultures received 0.1% DMSO.
Figure 3B:
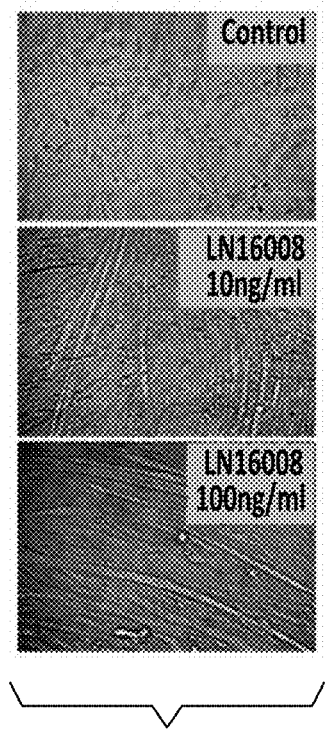
Figure 3C:
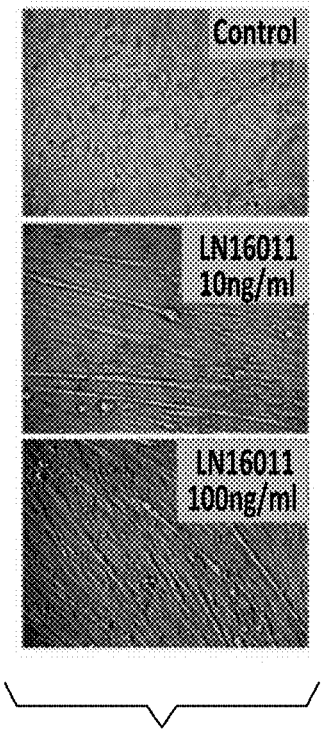
Figure 3D:
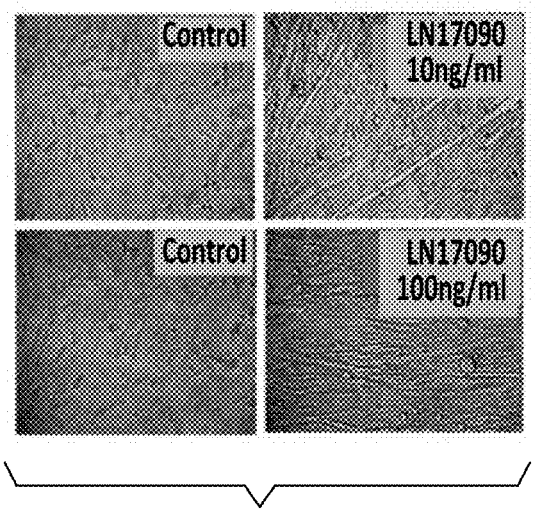
Figure 3E:
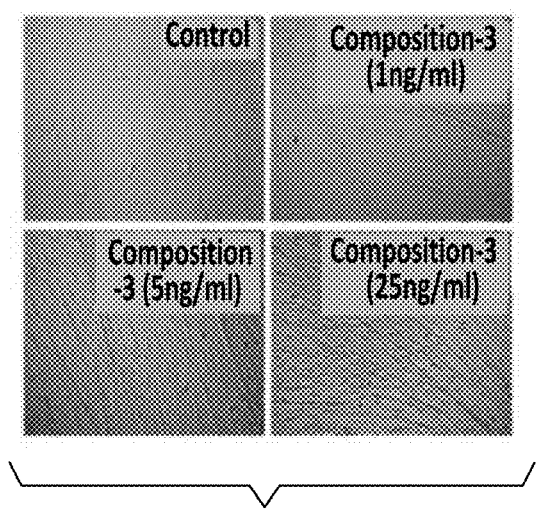

In addition, each one of the extracts of *Bauhinia racemosa* fruit (LN16002), *Cassia auriculata* aerial parts (LI17090), *Woodfordia fruticosa* tender stem (LN16008) and *Acacia nilotica* fruit (LN16011) activated mTOR by hyper-phosphorylation and increases the expression/production of muscle specific transcription factors such as MyoD and Myogenin in L6 rat skeletal myoblasts. This indicates increased muscle mass development via activation of ribosomal protein synthesis machinery and potentiating essential muscle specific myogenic growth factors. The modulation of said muscle specific markers by above extracts is depicted in FIGS. 1A to 1F. Further studies also indicated that treatment of L6 rat skeletal myoblasts with the extracts of *Bauhinia racemosa* fruit (LN16002), *Cassia auriculata* aerial parts (LN17090), *Woodfordia fruticosa* tender stem (LN16008) and *Acacia nilotica* fruit (LN16011) increases myotube formation through enhanced myogenesis as depicted in FIGS. 3A to 3E. These studies indicate that the said extracts have the potential to enhance the muscle tissue mass and increase the endurance levels.

Mitochondrial Membrane Potential:

Mitochondria are the primary source of ATP production. The voltage gradient across the inner mitochondrial membrane, which is called Mitochondrial membrane potential ($\Delta\psi_M$), is a key indicator of cellular health and injury/death. Under the conditions of oxidative stress, the membrane potential difference is reduced from its steady state level, which is called mitochondrial depolarization. Mitochondrial depolarization results in mitochondrial disruption, subsequently cell death. The efficacy of some of the extracts and compositions of the current invention to inhibit the mitochondrial depolarization or recover the cells/mitochondria from depolarized state back to polarized state was evaluated using FACS (Fluorescence Activated Cell Sorting) analyzer and Fluorescence probe JC-1 (5,5',6,6'-tetrachloro-1,1',3,3'-tetraethylbenzimidazolylcarbocyanine iodide)] on Flow Cytometer. For example, hydroalcohol extracts derived from *Mangifera indica* bark (LN16005), *Woodfordia fruticosa* tender stem (LN16008) and *Acacia nilotica* fruit (LN16011), and alcohol extract derived from *Cassia auriculata* aerial parts (LI17090) showed significant recovery from the depolarization caused to the membrane by hydrogen peroxide induced oxidative stress in L6 rat skeletal myoblasts as summarized in Table 14.

20S Proteasome Assay:

The Ubiquitin Proteasome Pathway (UPP) is the principal mechanism for protein catabolism in the mammalian cytosol and nucleus. The cytosolic 26S proteasome complex containing 20S (catabolic proteasome) and 19S (regulatory proteasome) protein subunits affects a wide variety of cellular processes and defects in the system can result in the pathogenesis of several important human diseases, which include muscular degeneration. The 20S proteasome is one of the important degradation pathways for protein degradation. The extract of *Cassia auriculata* (LN17090) exhibited potential to inhibit the 20S proteasome pathway in L6 rat myoblasts as summarized in FIG. 2F suggesting its use to reduce muscle wasting through inhibiting Ubiquitin Proteasome Pathway.

In an extension of the study, the extracts were converted into free flowing powder compositions by combining with excipients, carriers and diluents. The said compositions (Compositions-6 to 10) also show similar biological activities. Similarly, for exploring the feasibility of obtaining novel composition with improved efficacy at least two ingredients selected from the extracts or fractions derived from *Acacia nilotica* fruit, *Bauhinia racemosa* fruit, *Cassia auriculata* aerial parts, *Mangifera indica* bark, *Mangifera indica* leaves, and *Woodfordia fruticosa* tender stem; and some other plant parts of the same plants were combined to obtain novel compositions (Compositions-11 to 25 and 33 to 37), which were also tested for enhancement of nitric oxide/nitrite content, ATP and protein synthesis. Additionally, to further obtain a product with improved activity, at least one ingredient selected from the extracts or fractions derived from above plants were combined with at least one optional ingredient selected from the extracts or fractions derived from *Sphaeranthus indicus, Rubia cordifolia* and *Punica granatum* at different ratios and the compositions so obtained (Compositions-2 to 5 and Compositions-26 to 32) were tested for the modulation of nitric oxide and ATP.

Unexpectedly, these compositions (Compositions-2 to 5 and Compositions-11 to 37) showed better efficacy in enhancing nitric oxide, ATP and protein synthesis, when compared to their corresponding individual ingredients suggesting the tendency of the extracts to show synergism when combined with other ingredients. For example, the rat L6skeletal muscle cells treated with hydroalcohol extract of *Mangifera indica* extract (LN16005) at 2.5 ng/mL concentration and *Sphaeranthus indicus* extract (LN16015) at 7.5 ng/mL concentration showed 3.52% and 6.28% increase in levels of ATP respectively. The cells treated with composition-2 containing these two extracts in 1:3 ratio showed 22.2% increase in ATP level at 10 ng/mL, which is significantly better than the additive effect (9.78%) derived for the same concentration. Similarly, the rat L6skeletal muscle cells treated with composition-3 containing the same ingredients in 1:2 showed 60.25% increase in nitrite production at 1 µg/mL concentration, when compared to 5.71% and 4.83% increase shown by the hydroalcohol extract of *Mangifera indica* extract (LN16005) and *Sphaeranthus indicus* extract (LN16015) at 0.33 µg/mL and 0.66 µg/mL respectively. Hence, the observed increase in nitrite production induced by composition-3 at 1 µg/mL concentration is much higher (60.25%) compared to the corresponding additive effect shown by the individual ingredients (10.74%). The data for elevation of Nitrite levels and ATP for compositions-2 to 5 and the corresponding two individual ingredients is summarized in tables 2 and 6. The data suggests that the compositions containing the extracts derived *Mangifera indica* and *Sphaeranthus indicus* exhibit synergistic efficacy in increasing the ATP and nitrite levels. In addition, the composition-3 dose dependently increases the NADPH oxidase activity with an IC50 value of 216 ng/mL. It also dose dependently enhanced protein content in L6 rat skeletal myoblast cells. Composition-3 increases myogenesis (myotube formation) via myotube formation in C2C12 mesenchymal myoblasts (FIG. 3E), supporting its potential in building skeletal muscle fibers. It activates protein synthesis via activating mTOR signaling in skeletal muscle cells and up-regulating Muscle Specific Transcription Factors (Myf6, MyoD and Myogenin) in L6 Skeletal Muscle Cells as summarized in FIGS. 1E to 1F. Composition-3 further improves mitochondrial function via mitochondrial biogenesis (Table 12) and up-regulating key enzyme protein, Cyt C oxidase-1 (COX1), of mitochondrial Oxidative Phosphorylation (OX-PHOS) pathway as summarized in FIG. 2F. In addition, the composition-3 exhibited potential to inhibit the 20S proteasome pathway in L6 rat myoblasts as summarized in FIG. 2F suggesting its potential to protect from muscle wasting. Importantly, composition-3 also showed significant recovery from the depolarization caused to the membrane by hydrogen peroxide induced oxidative stress in L6 rat skeletal myoblasts as summarized in table 14.

The data for the synergistic efficacy of other compositions (Composition-11 to Composition-25) to elevate the nitrite levels are summarized in tables 3 and 4; and the synergistic efficacy to increase the ATP levels is summarized in tables 7 to 11. Similarly, the synergistic efficacy of compositions-26 to 31 to increase the mitochondrial biogenesis is summarized in tables 12, 13 and 13A.

The efficacy of the extracts derived from *Bauhinia racemosa* fruit, *Mangifera indica* bark, *Woodfordia fruticosa* and *Acacia nilotica* fruit tender stem or their compositions for enhancing energy and endurance was further evaluated in an animal study. For illustration, Swiss albino mice were orally treated with vehicle or 200 mg of LN16011 or the composition-1 [containing 80% methanol extract of *Mangifera indica* bark (LN16014) and *Sphaeranthus indicus* extract (LN16015)] for 21 days. On day 21, one hour after the treatment the mice were subjected to forced-swim test and the activity monitored using the SMART video tracking system (Panlab S.L.U). The animals treated with the extract LN16011 or composition-1 showed reduced resting time and enhanced slow moving time, fast moving time, total moving time, path length of swimming and average velocity compared to the control treated animals as summarized in table 15.

Similarly, after 21 days of treatment, the grip strength of mice was measured by using Grip strength meter (UgoBasile, Italy). The animals supplemented with the compositions LN16011 and composition-1 showed improved grip strength compared to the animals treated with the control as summarized in Table 16.

In a similar experiment, the efficacy of composition-33 to 37 containing two ingredients selected from the extracts of the plant parts of *Mangifera indica, Acacia nilotica* and *Cassia auriculata* were evaluated for enhancing energy and endurance in a similar model. Oral supplementation of these test or reference product for 21 days showed clear improvement in swimming parameters and grip strength in mice. Supplementation of Composition-33, Composition-34, Composition-35, Composition-36, Composition-37 and L-carnitine resulted in remarkable increase in swimming distance, remarkable increase in swimming time and clear decrease in resting time. In addition, the mice supplemented with Composition-33, Composition-34, Composition-36, Composition-37 and L-carnitine also showed statistically significant (P<0.05) increase in grip strength over vehicle control group. Composition-35 also showed significant improvement in grip strength. The results are summarized tables 17 and 18. This data supports the potential of the novel compositions of the current invention for increasing the energy and muscle strength.

Efficacy of the ethanol extract of *Cassia auriculata* aerial parts (LN17090) and *Acacia nilotica* fruit (LN16011) in improving Grip strength, Muscle endurance, and Muscle fiber diameter size in Dexamethasone induced Sarcopenia model of Sprague Dawly (SD) rats was studied. The animals in dexamethasone supplemented Sarcopenia Group (G2) showed significant reduction in grip strength, muscle endurance and muscle fiber diameter when compared to those in the normal control group (G1) as shown in FIGS. 4A to 4D suggesting the successful induction of Sarcopenia. The treatment groups supplemented 200 mg of LN17090 (G3) and 400 mg of LN17090 (G4) showed dose dependent and statistically significant improvement in grip strength compared to the disease control group (G2). Animals supplemented with LN16011 (G5) and HMB (G6) also showed significant improvement in grip strength as summarized in FIGS. 4A to 4D. Similarly, rats supplemented with LN17090 (G3 and G4) showed significant improvement in muscle endurance over disease control group (G2). Clear improvement in muscle endurance was also observed in rats supplemented with LN16011 (G5). Finally, when compared to disease control group (G2) rats supplemented with LN17090 (G3 and G4) showed dose dependent and statistically significant improvement in both gastrocnemius and soleus muscle fiber diameter. Animals supplemented with LN16011 and HMB (G4 and G5) also showed significant improvement in muscle fiber diameter. The data is summarized in-FIGS. 4A to 4D. Overall the data suggests that the extracts of *Cassia auriculata* leaves (LN17090) and *Acacia nilotica* (LN16011) can provide effective supplements to treat Sarcopenia.

The forgoing demonstrates that extracts or fractions derived from *Acacia nilotica, Bauhinia racemosa, Cassia auriculata, Mangifera indica*, and *Woodfordia fruticosa* and their compositions could be potent natural supplements to provide an onset, steady maintenance of energy, increasing energy levels, muscle growth, muscle strength, physical endurance and mental alertness, and treating sarcopenia and muscular atrophy in humans and animals.

Accordingly, in a preferred embodiment the present invention discloses extracts and fraction derived from *Acacia nilotica, Bauhinia racemosa, Cassia auriculata, Mangiferaindica* and *Woodfordia fruticosa* either alone or their compositions useful for increasing energy levels, endurance, muscle mass, muscle strength and mental alertness, and for the effective treatment of sarcopenia and muscular atrophy.

In another embodiment the invention discloses extracts and fractions derived from *Acacia nilotica, Bauhinia racemosa, Cassia auriculata, Mangiferaindica* and *Woodfordia fruticosa* and their compositions for the onset and steady maintenance of energy, muscle strength and mental alertness, wherein, the extracts or fractions and their compositions are useful for enhancing muscle strength, physical activity, physical fitness, mental alertness, energy levels, stamina levels, circulatory health, blood vessel health or for better physical and mental health in a mammal.

In another embodiment, the invention discloses compositions comprising extracts and fractions derived from *Acacia nilotica, Bauhinia racemosa, Cassia auriculata, Mangifera indica* and *Woodfordia fruticosa* in combination with at least one biologically active ingredient selected from plant extracts, fraction or pure phytochemicals, minerals, vitamins as a natural energy enhancer to provide an onset and steady maintenance of energy, muscle strength and mental alertness in a warm blooded animal or mammal in need thereof.

In another embodiment, the invention discloses compositions comprising extracts and fractions derived from *Acacia nilotica, Bauhinia racemosa, Cassia auriculata, Mangifera indica* and *Woodfordia fruticosa* in combination with at least one biologically active ingredient selected from extracts, fraction or pure phytochemical, derived from at least one plant species selected *Sphaeranthus indicus, Rubia cordifolia, Punica granatum, Coleus aromaticus, Cissus quadrangularis, Curcuma longa, Garcinia mangostana, Citrulus lanatus, Oscimun sanctum, Cinnamomum tamala, Ocimum basilicum, Zingiber officinalis, Tribulus terrestris, Trachypermum ammi, Mentha arvensis* and *Foeniculumvulgare* for increasing energy levels, endurance, muscle mass, muscle strength mental alertness and for treating sarcopenia and muscular atrophy.

In another embodiment, the invention discloses compositions comprising extracts and fractions derived from *Acacia nilotica, Bauhinia racemosa, Cassia auriculata, Mangifera indica* and *Woodfordia fruticosa* in combination with at least one biologically active ingredient selected from the extracts, fraction or pure phytochemicals, derived from at least one plant part of *Sphaeranthus indicus* for increasing energy levels, endurance, muscle mass, muscle strength and mental alertness.

In yet another embodiment, the invention discloses compositions comprising extracts and fractions derived from *Acacia nilotica, Bauhinia racemosa, Cassia auriculata, Mangifera indica* and *Woodfordia fruticosa* in combination with at least one ingredient selected from excipients, carriers, diluents, sweeteners, flavorants colorants, vitamins, proteins or amino acids, as a natural energy enhancer for enhancing physical or mental performance, onset and steady maintenance of energy enhancing physical activity, physical fitness, mental alertness, energy levels, stamina levels, circulatory health, blood vessel health or for better mental health in a mammal.

In another embodiment, the invention discloses extracts and fractions derived from *Acacia nilotica, Bauhinia racemosa, Cassia auriculata, Mangifera indica* and *Woodfordia fruticosa* or their compositions for improved physical performance, which include increased stamina and improved speed, strength, power, endurance, flexibility, agility, balance, focus coordination, reaction time, fatigue recovery and also increase of sex stamina. Examples of improved mental performance include improved sharpness, attention span, mental alertness, cognitive functions, mood elevation, and recovery or reduction of mental fatigue (e.g., following a high-intensity physical exercise), for treating muscle wasting (Sarcopenia) and mitochondrial dysfunction.

In another embodiment, the inventive compositions include dietary supplements, food ingredient formulations such as beverages, snacks and energy drinks containing the above said ingredient(s) or its composition(s) for enhancing, muscle strength, physical activity, physical fitness, mental alertness, energy levels, stamina levels, circulatory health, blood vessel health or for better mental health in warm blooded animals in need thereof.

In another embodiment, the invention provides a method of increasing natural energy to provide an onset and steady maintenance of energy, mental alertness, muscle strength and increasing muscle mass in a mammal, wherein the method comprises supplementing or treating the said mammal with at least one ingredient selected from the extracts and fractions derived from *Acacia nilotica, Bauhinia racemosa, Cassia auriculata, Mangifera indica* and *Woodfordia fruticosa* or their compositions.

In yet another embodiment, the invention provides compositions comprising at least two ingredients selected from the herbal extracts or fractions derived from *Acacia nilotica, Bauhinia racemosa, Cassia auriculata, Mangiferaindica* and *Woodfordia fruticosa* as natural enhancers of energy, muscle mass, muscle power and physical performance in warm blooded animals in need thereof.

In yet another embodiment the invention provides compositions comprising said biologically active ingredients as described in accordance with the present invention, in combination with one or more components selected from extract(s), fraction(s), active compound(s), phytochemical(s); powder(s) derived from plant(s), animal(s) or microorganisms with proven therapeutic health benefits; pharmaceutically or dietetically acceptable agents, active ingredients, vitamins, amino acids or minerals.

In a further exemplary embodiment, the composition of the present invention may further contain optionally one or more of the non-limiting components such as vitamins selected from B vitamins, including thiamine, riboflavin, niacin, pantothenic acid, pyridoxine, biotin, cyanocobalamin, choline and/or folic acid, including the reduced forms of folic acid such as but not limited to folinic acid, calcium folinate and methyl tetrahydrofolate. The B-complex vitamins are also water soluble vitamins that aid the breakdown of carbohydrates into glucose to provide energy for the body, the breakdown of fats and proteins to aid the normal functioning of the nervous system, and muscle tone in the stomach and intestinal tract. Particular forms of B vitamins in the composition may include d-Calcium pantothenate, niacinamide, pyridoxine hydrochloride, and thiamine mononitrate; or amino acids.

In another embodiment the said herbal extracts or fractions or their composition(s) can be taken e.g. by performance athletes, those engaged in endurance and multi-discipline sports, aged and sick persons in order to increase mental alertness, stamina levels, muscle strength, physical fitness and to maintain the onset and steady maintenance of energy, muscle strength. The present ingredients and compositions may be formulated as a "fitness supplement" or "fitness drink" that can be taken with breakfast or in the form of a concentrate from which such a drink can be regularly used.

The composition wherein, the concentration of *Acacia nilotica, Bauhinia racemosa, Cassia auriculata, Mangifera indica* and *Woodfordia fruticosa* derived ingredients in the composition individually or jointly varies from 0.01% to 99.99%.

In another embodiment, the invention provides a method of ameliorating the biomarkers selected from ATP, Nitric Oxide, eNOS, mTOR, MyoD and Myogenin and method of enhancing the biological processes selected from mitochondrial biogenesis, myogenesis, muscle cell proliferation wherein the method comprises administering to a subject or mammal or warm blooded animal a therapeutically effective quantity of the extracts and fractions derived from *Acacia nilotica, Bauhinia racemosa, Cassia auriculata, Mangifera indica* and *Woodfordia fruticosa* or their compositions which contain optionally at least one biologically active ingredient selected from the plants extracts or fractions.

In another embodiment of the invention the various suitable solvents that can be used for preparing the extracts and fractions or extracting or fractionating the herbs *Acacia nilotica, Bauhinia racemosa, Cassia auriculata, Mangifera indica* and *Woodfordia fruticosa* include but not limited to C1-C5 alcohols, like ethanol, methanol; water and mixtures thereof; C1-C7 hydrocarbons such as hexane; esters like ethyl acetate and the like and mixtures thereof.

In another embodiment of the invention, the plant parts for preparing the extracts can be selected from leaves, stems, tender stem, aerial parts, fruit, fruit rind, seed, flower heads, root, bark or whole plant or mixtures thereof.

In another embodiment, the extracts or fractions or composition(s) of the present invention may be formulated in dry form, liquid form, food product, dietary supplement or any suitable form such as tablet, a capsule or a soft chew.

In another embodiment, the extracts or fractions or composition(s) can be delivered in the form of controlled release tablets, using controlled release polymer-based coatings by the techniques including nanotechnology, microencapsulation, colloidal carrier systems and other drug delivery systems.

In another embodiment of the invention provides the extracts or fractions or composition(s) as nutritional/dietary supplements that can be contemplated/made in the dosage form of healthy foods, or food for specified health uses such as solid food like chocolate or nutritional bars, semisolid food like cream or jam, or gel and also beverage and the like, such as refreshing beverage, lactic acid bacteria beverage, drop, candy, chewing gum, gummy candy, yoghurt, ice cream, pudding, soft adzuki bean jelly, jelly, cookie, tea, soft drink, juice, milk, coffee, cereal, snack bar and the like.

In other embodiments, the extracts or fractions or composition(s) of this invention are useful in treating mitochondrial deficiencies in both humans and animals. It also can be used for enhancing or maintaining physical or mental performance, reducing infection in physically stressed athletes or non-athletes from intense physical exercises.

In another exemplary embodiment the inventive extracts and fractions derived from *Acacia nilotica, Bauhinia racemosa, Cassia auriculata, Mangifera indica*, and *Woodfordia fruticosa* or their compositions can further be combined optionally with one or more pharmaceutically or dietetically acceptable excipients, carriers and diluents, which include but not limited to glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, proteins, calcium salts, pigments, flavors, preservatives, distilled water, saline, aqueous glucose solution, alcohol, propylene glycol and polyethylene glycol, various animal and vegetable oils, white soft paraffin, paraffin, flavorants, colorants and wax.

In still another embodiment, the invention features a method of enhancing physical or mental performance, steady maintenance of energy, physical endurance, muscle mass, muscle strength and mental alertness in humans and animals, wherein the method comprises administering to a subject in need thereof an effective amount of an extract and fraction derived from *Acacia nilotica, Bauhinia racemosa, Cassia auriculata, Mangifera indica*, and *Woodfordia fruticosa* or their compositions, wherein examples of improved physical performance include increased stamina and improved speed, strength, power, endurance, flexibility, agility, balance, focus coordination, reaction time, fatigue recovery and also increase of sex stamina.

Examples of improved mental performance include improved sharpness, attention span, mental alertness, cognitive functions, mood elevation, and recovery or reduction of mental fatigue (e.g., following a high-intensity physical exercise).

Those of ordinary skill in the art will appreciate that changes could be made to the embodiments described above without departing from the broad inventive concept thereof. It is understood, therefore, that this invention is not limited to the particular embodiments or examples disclosed, but is intended to cover modifications within the objectives and scope of the present invention as defined in the specification. The presented examples illustrate the invention, but they should not be considered to limit the scope of the invention in any way.

EXAMPLES

Example 1

Preparation of water extracts of dried raw materials of *Bauhinia racemosa* fruit, *Cassia auriculata* aerial parts, *Mangifera indica* stem bark, *Woodfordia fruticosa* tender stem and *Acacia nilotica* fruit: The raw materials of 100 g each of *Bauhinia racemosa* fruit, *Mangifera indica* stem bark, *Woodfordia fruticosa* tender stem and *Acacia nilotica* fruit were pulverized and the powders extracted individually with water (600 mL) using continuous percolation at ambient temperature for 1.5 h in soxhlet apparatus. The extract was removed from Soxhlet and the spent raw material was re-extracted twice with water (2×300 mL) under similar conditions. The combined extract from each raw material was fine filtered and concentrated on a rotary evaporator and the concentrate was subjected to final drying on freeze dryer to obtain the water extracts of *Bauhinia racemosa* fruit (LN16001; 5.15 g), *Cassia auriculata* aerial parts (LN17088; 10.5 g), *Mangiferaindica* stem bark (LN16004; 9.9 g), *Woodfordia fruticosa* tender stem (LN16007; 3.85 g) and *Acacia nilotica* fruit (LN16010; 38.6 g).

Example 2

Preparation of hydroalcohol (aqueous ethanol) extracts of dried raw materials of *Bauhinia racemosa* fruit, *Cassia auriculata* aerial parts, *Mangifera indica* stem bark, *Mangifera indica* stem leaves, *Woodfordia fruticosa* tender stem and *Acacia nilotica* fruit:

The raw materials of 100 g each of *Bauhinia racemosa* fruit, *Cassia auriculata* aerial parts, *Mangiferaindica* stem bark, *Mangifera indica* leaves, *Woodfordia fruticosa* tender stem and *Acacia nilotica* fruit were pulverized and the powders extracted individually with 50% ethanol (600 mL) using continuous percolation at ambient temperature for 1.5 h in soxhlet apparatus. The extract was removed from Soxhlet and the spent raw material was re-extracted twice with 50% ethanol (2×300 mL) under similar conditions. The combined extract from each raw material was fine filtered and concentrated on a rotary evaporator and the concentrate was subjected to final drying on freeze dryer to obtain the hydroalcohol extracts of *Bauhinia racemosa* fruit (LN16002; 6.70 g), *Cassia auriculata* aerial parts (LN17089; 11.6 g), *Mangifera indica* stem bark (LN16005; 17.3 g), *Mangifera indica* leaves (LN17093; 14.9 g), *Woodfordia fruticosa* tender stems (LN16008; 6.0 g) and *Acacia nilotica* fruit (LN16011; 44.0 g).

Example 3

Preparation of ethanol extracts of dried raw materials of *Bauhinia racemosa* fruit, *Cassia auriculata* aerial parts, *Mangifera indica* stem bark, *Woodfordia fruticosa* tender stem and *Acacia nilotica* fruit:

The raw materials of 100 g each of *Bauhinia racemosa* fruit, *Cassia auriculata* aerial parts, *Mangifera indica* stem bark, *Woodfordia fruticosa* tender stem and *Acacia nilotica* fruit were pulverized and the powders extracted individually with ethanol (600 mL) using continuous percolation at ambient temperature for 1.5 h in soxhlet apparatus. The extract was removed from Soxhlet and the spent raw material was re-extracted twice with ethanol (2×300 mL) under similar conditions. The combined extract from each raw material was fine filtered and concentrated on a rotary evaporator to obtain the ethanol extracts of *Bauhinia racemosa* fruit (LN16003; 2.67 g), *Cassia auriculata* aerial parts (LN17090; 8.4 g), *Mangifera indica* stem bark (LN16006; 9.55 g), *Woodfordia fruticosa* tender stems (LN16009; 6.3 g) and *Acacia nilotica* fruit (LN16012; 24.9 g).

Example 4

Preparation of 80% methanol extract of *Mangifera indica* bark: *Mangifera indica* bark (100 g) was pulverized and the powder was charged into a lab extractor or and extracted with 80% methanol (500 mL) at reflux temperature for 2 h. The extract was filtered and the spent raw material was re-extracted twice with 80% methanol (2×400 mL) under similar conditions. The combined extract was fine filtered and concentrated under vacuum to obtain a residue (LN16014; 12.5 g).

b) Preparation of 80% methanol extract of *Mangifera indica* leaf:

*Mangifera indica* leaf (100 g) was pulverized and the powder was charged into a lab extractor or and extracted with 80% methanol (500 mL) at reflux temperature for 2 h. The extract was filtered, and the spent raw material was re-extracted twice with 80% methanol (2×400 mL) under similar conditions. The combined extract was fine filtered and concentrated under vacuum to obtain a residue (LN17091); 12.5 g).

c) Preparation of 80% methanol extract (LN17094) of *Acacia nilotica* fruit: The 80% methanol extract of *Acacia nilotica* fruit was prepared using the same procedure described above.

d) Preparation of the representative extracts from other plant parts and other solvent extraction medium: The *Acacia nilotica* fruit rind hydroalcohol extract (LN17095), *Acacia nilotica* fruit methanol extract (LN17096), *Acacia nilotica* fruit acetone extract (LN17097), *Bauhinia racemosa* fruit rind hydroalcohol extract (LN17109), *Bauhinia racemosa* seed hydroalcohol extract (LN17098), *Cassia auriculata* leaf water extract (LN17099), *Cassia auriculata* leaf hydroalcohol extract (LN17100), *Cassia auriculata* leaf acetone extract (LN17101), *Cassia auriculata* stem ethanol extract (LN17106), *Woodfordia fruticosa* leaf ethanol extract (LN17102), *Woodfordia fruticosa* leaf acetone extract (LN17103), *Mangifera indica* leaf hydroalcohol extract (LN17093), *Mangifera indica* leaf methanol extract (LN17094), *Mangifera indica* bark acetone extract (LN17095) were prepared using the extraction procedures disclosed above.

Example 5

Preparation of methanol, aqueous alcohol (60% methanol) and water extracts of *Punica granatum* dried fruit rind:

*Punica granatum* fruit rind (100 g) was pulverized and the powder was charged into a lab extractor and extracted with methanol (400 mL) at 80° C. temperature for 2 h. The extract was filtered, and the spent raw material was re-extracted twice with methanol (2×300 mL) under similar conditions. The combined extract was fine filtered and concentrated under vacuum to obtain a residue of methanol extract (LN16048; 25.6 g). The aqueous methanol extract (LN16047) and water extract (LN16046; 28.6 g) were obtained by adopting similar procedure using 60% methanol and water as extraction solvents respectively.

Example 6

Aqueous extract of *Rubia cordifolia*: Dried roots of the *Rubia cordifolia*, (100 g) were pulverized to coarse powder, extracted with 500 mL of water at 70-80° C. for 1 hr. Extraction process was repeated twice using 300 mL of water. All the extracts were combined, the combined aqueous extract was fine filtered, and the clear extract was evaporated to dryness on a climbing film evaporator at 50-60° C. to obtain a residue (10 g)

Example 7

Preparation of *Sphaeranthus indicus* extract. The *Sphaeranthus indicus* flower heads (100 g) raw material (R1\4)

was pulverized and the powder was extracted ethanol (700 mL) at ambient temperature using percolation techniques. The extraction process was repeated two more times with 500 mL ethanol each time. The extracts were combined, the combined extract fine filtered and concentrated at 45-50° C. under vacuum. The residue was portioned between water and ethyl acetate and the layers were concentrated separately to obtain ethyl acetate fraction and water fraction. The ethyl acetate fraction and water fraction so obtained were combined 3:1 ratio to obtain *Sphaeranthus indicus* extract (LN16015). However, any organic solvent extract/fraction or blend containing the extracts/fractions at any other ratio can also be used.

The above extraction procedures are for illustration purpose only. Other plant parts can also be extracted using similar procedures. The extraction techniques and other extraction solvents can also be used. The extraction parameters such as temperature, pressure and solvent ratios can also be varied.

Example 8

Preparation of selected compositions comprising *Acacia nilotica, Bauhinia racemosa, Mangifera indica, Woodfordia fruticosa* and *Sphaeranthus indicus* extracts.

Composition-1: The composition-1 was prepared by combining 22 g of 80% alcohol extract of *Mangifera indica* (LN16014) and 44 g of *Sphaeranthus indicus* extract (LN16015), 28 g of Microcrystalline cellulose powder (MCCP) and 2 g of Syloid.

Composition-2: The composition-3 was prepared by combining the hydroalcohol extract of *Mangifera indica* (LN16005) and extract of *Sphaeranthus indicus* (LN16015) in the ratio of 1:3.

Composition-3: The composition-2 was prepared by combining the hydroalcohol extract of *Mangifera indica* bark (LN16005) and extract of *Sphaeranthus indicus* flower heads (LN16015) in the ratio of 1:2.

Composition-4: The composition-4 was prepared by combining the hydroalcohol extract of *Mangifera indica* (LN16005) and extract of *Sphaeranthus indicus* (LN16015) in the ratio of 1:1.

Composition-5: The composition-5 was prepared by combining the hydroalcohol extract of *Mangifera indica* (LN16005) and extract of *Sphaeranthus indicus* (LN16015) in the ratio of 2:1.

Composition-6: The composition-6 was prepared by combining the hydroalcohol extract of *Mangifera indica* bark (LN16005) and microcrystalline cellulose powder in 3:1 ratio.

Composition-7: The composition-7 was prepared by combining the 80% methanol extract of *Mangifera indica* leaves (LN17091) and microcrystalline cellulose powder in 3:1 ratio.

Composition-8: The composition-8 was prepared by combining the hydroalcohol extract of *Acacia nilotica* fruit (LI16011) and microcrystalline cellulose powder in 3:1 ratio.

Composition-9: The composition-9 was prepared by combining the hydroalcohol extract of *Woodfordia fruticosa* tender stem (LI16008) and microcrystalline cellulose powder in 3:1 ratio.

Composition-10: The composition-10 was prepared by combining the alcohol extract of *Cassia auriculata* (LN17090) and microcrystalline cellulose powder in 3:1 ratio.

Compositions-11, 12 and 13 containing *Mangifera indica* bark hydroalcohol extract (LN16005) and hydroalcohol extract of *Acacia nilotica* fruit (L116011). The Compositions-11, 12 and 13 were prepared by combining the hydroalcohol extract of *Mangifera indica* (LN16005) and hydroalcohol extract of *Acacia nilotica* fruit (LI16011) at 1:2, 1:1 and 2:1 ratios respectively.

Compositions-14, 15 and 16 containing 80% methanol extract of *Mangifera indica* leaves (LN17091) and hydroalcohol extract of *Acacia nilotica* fruit (L116011). The Compositions-14, 15 and 16 were prepared by combining the 80% methanol extract of *Mangifera indica* leaves (LN17091) and hydroalcohol extract of *Acacia nilotica* fruit (LI16011) at 1:2, 1:1 and 2:1 ratios respectively.

Compositions-17, 18 and 19 containing *Mangifera indica* bark hydroalcohol extract (LN16005) and alcohol extract of *Cassia auriculata* (LN17090). The Compositions-17, 18 and 19 were prepared by combining the hydroalcohol extract of *Mangifera indica* (LN16005) and alcohol extract of *Cassia auriculata* (LN17090) at 1:2, 1:1 and 2:1 ratios respectively.

Compositions-20, 21 and 22 containing 80% methanol extract of *Mangifera indica* leaves (LN17091) and alcohol extract of *Cassia auriculata* (LN17090). The Compositions-20, 21 and 22 were prepared by combining the 80% methanol extract of *Mangifera indica* leaves (LN17091) and alcohol extract of *Cassia auriculata* (LN17090) at 2:1, 1:1 and 1:2 ratios respectively.

Compositions-23, 24 and 25 containing alcohol extract of *Cassia auriculata* (LN17090) and hydroalcohol extract of *Acacia nilotica* fruit (L116011). The Compositions-23, 24 and 25 were prepared by combining the alcohol extract of *Cassia auriculata* (LN17090) and hydroalcohol extract of *Acacia nilotica* fruit (LI16011) at 2:1, 1:1 and 1:2 ratios respectively.

Compositions-26, 27, 28 and 29 containing alcohol extract of *Cassia auriculata* (LN17090) and methanol extract of *Punica granatum* fruit (LN16048). The Compositions-26, 27, 28 and 29 were prepared by combining the alcohol extract of *Cassia auriculata* (LN17090) and methanol extract of *Punica granatum* fruit (LN16048) at 2:1, 1:1, 1:2 and 1:3 ratios respectively.

Compositions-30, 31 and 32 containing alcohol extract of *Cassia auriculata* (LN17090) and water extract of *Rubia cordifolia* root (LN17092). The Compositions-30, 31 and 32 were prepared by combining the alcohol extract of *Cassia auriculata* (LN17090) and water extract of *Rubia cordifolia* root (LN17092) at 3:1, 1:1 and 1:2 ratios respectively.

Compositions-33: The Composition-33 was prepared by combining the 80% methanol extract of *Mangifera indica* bark (LN16014) and hydroalcohol extract of *Acacia nilotica* (LN16011) at 1:1 ratio.

Compositions-34: The Composition-34 was prepared by combining the 50% ethanol extract of *Mangifera indica* leaves (LN17093) and 80% methanol extract of *Acacia nilotica* (LN17094) at 1:1 ratio.

Compositions-35: The Composition-35 was prepared by combining the 50% ethanol extract of *Mangifera indica* leaves (LN17093) and 50% ethanol extract of *Cassia auriculata* (LN17089) at 1:2 ratio.

Compositions-36: The Composition-36 was prepared by combining the 80% methanol extract of *Mangifera indica* bark (LN16014) and 50% ethanol extract of *Cassia auriculata* (LN17089) at 1:2 ratio.

Composition-37: The Compositions-37 was prepared by combining the hydroalcohol extract of *Cassia auriculata* (LN17089) and hydroalcohol extract of *Acacia nilotica* fruit (L116011) at 1:1 ratio.

Example 9

Evaluation of extracts of *Bauhinia racemosa* fruit (LN16002), *Mangifera indica* stem bark (LN16005 and LN16014), *Woodfordia fruticosa* tender stem (LN16008),

*Acacia nilotica* fruit (LN16011 and LN16012) and *Sphaeranthus indicus* extract (LN16015) for induction of Nitrite: To evaluate whether the test sample can induce nitric oxide generation in human endothelial cells, we tested nitrite concentration in the cell culture supernatants of EA.hy926 human endothelial cells (ATCC, Manassas, Va.). Briefly, equal number of EA.hy926 human endothelial cells (1.5× $10^5$) was plated in 35 mm culture dish. After attachment of the cells, the culture dishes were washed twice with phosphate buffered saline and the washed cells were treated with different concentrations of test samples LN16002, LN16005, LN16008, LN16011, 16012, LN16014 and LN16015 for 4 h. The vehicle control cultures received 0.2% DMSO. The cell free culture supernatants were collected and nitrite content was estimated using Griess assay. Fifty micro liters of culture supernatants were mixed with equal volume of Griess reagent (a mixture containing 1:1 ratio of 0.2% naphthylene diaminedihydrochloride and 2% sulphanilamide in 5% phosphoric acid) in each well of a micro-titer plate and incubated further for 10 min in room temperature. The color development was measured at 550 nm in a Microplate reader (Spectra MaxM5, Molecular devices, Sunnyvale, Calif.). Standard curves were constructed with known concentrations of sodium nitrite. The percentage increase in nitrite concentration was calculated and the data is summarized table 1. The nitrite data obtained for extracts derived from other plant parts and those derived using other solvent media for extraction are also summarized in table-1 respectively.

TABLE 1

| S. No. | Name of the herb | Extract Code | % increase in Nitrite conc. at 2.5 µg/mL | % increase in Nitrite conc. at 5.0 µg/mL |
|---|---|---|---|---|
| 1 | *Mangifera indica* bark hydroalcohol extract | LN16005 | 48.8 | 58.3 |
| 2 | *Woodfordia fruticosa* hydroalcohol extract | LN16008 | 45.7 | 50.2 |
| 3 | *Acacia nilotica* hydroalcohol extract | LN16011 | 73.5 | 79.1 |
| 4 | *Acacia nilotica* alcohol extract | LN16012 | 75.6 | 79.9 |
| 5 | *Mangifera indica* bark 80% methanol extract | LN16014 | 51.5 | 62.4 |
| 6 | *Casssia auriculata* ethanol extract | LN17090 | 23.6 | 38.3 |
| 7 | *Acacia nilotica* fruit water extract | LN16010 | — | 62.16 |
| 8 | *Acacia nilotica* fruit rind hydro alcohol extract | LN17095 | — | 44.14 |
| 9 | *Acacia nilotica* fruit methanol extract | LN17096 | — | 57.01 |
| 10 | *Acacia nilotica* fruit Acetone extract | LN17097 | — | 18.4 |
| 11 | *Bauhinia racemosa* fruit rind hydro alcohol extract | LN16002 | — | 44.96 |
| 12 | *Bauhinia racemosa* seed hydro alcohol extract | LN17098 | — | 45.69 |
| 13 | *Cassia auriculata* leaf water extract | LN17099 | — | 17.73 |
| 14 | *Cassia auriculata* leaf hydro alcohol extract | LN17100 | — | 77.6 |
| 15 | *Cassia auriculata* leaf acetone extract | LN17101 | — | 38.81 |
| 16 | *Woodfordia fruticosa* leaf ethanol extract | LN17102 | — | 129.02 |
| 17 | *Woodfordia fruticosa* leaf acetone extract | LN17103 | — | 100.45 |
| 18 | *Mangifera indica* bark water extract | LN16004 | — | 69.73 |

Example 10

Evaluation of Compositions-2 to 32 for induction of Nitrite in EA.hy926 human endothelial cells: The study was done using procedure described above in Example 9. The percentage increase in nitrite concentration for different compositions was calculated and the data is summarized in tables 2 to 4.

TABLE 2

Nitrite Assay (1 µ/ml)

| | LN16005 | | LN16015 | | | % increase | % increase |
|---|---|---|---|---|---|---|---|
| Test sample | µg/mL | % increase | µg/mL | % increase | Ratio | Additive (calculated) | Observed at 1 µ/ml |
| Composition-2 | 0.25 | 4.33 | 0.75 | 5.49 | 1:3 | 9.82 | 32.84 |
| Composition-3 | 0.33 | 5.71 | 0.66 | 4.83 | 1:2 | 10.54 | 60.25 |
| Composition-5 | 0.66 | 11.43 | 0.33 | 2.41 | 2:1 | 13.84 | 79.72 |

TABLE 3

Nitrite assay (5 µg/ml)

| | LN16005 | | LN16011 | | | % increase | % increase |
|---|---|---|---|---|---|---|---|
| Test sample | µg/ml | % increase | µg/ml | % increase | Ratio | Additive (calculated) | Observed at 5 ng/ml |
| Composition-12 | 2.5 | 00 | 2.5 | 16.12 | 1:1 | 16.12 | 23.82 |
| Composition-13 | 3.4 | 00 | 1.6 | 10.31 | 2:1 | 10.31 | 35.53 |

TABLE 4

| | Nitrite Assay (2.5 μg/ml) | | | | | |
|---|---|---|---|---|---|---|
| | LN16005 | | LN17090 | | | % increase |
| | | | | | % increase | Observed |
| | | % | | % | Additive | at |
| Test sample | μg/ml | increase | μg/ml | increase | Ratio | (calculated) | 2.5 μg/ml |
| Composition-19 | 1.66 | 21.05 | 0.83 | 00 | 2:1 | 21.05 | 24.39 |

Example 11

ATP assay: Evaluation of the ATP enhancing efficacy of the hydroalcohol extracts of *Bauhinia racemosa* fruit (LN16002), *Mangifera indica* stem bark (LN16005 and LN16014), *Woodfordia fruticosa* tender stem(LN16008), *Acacia nilotica* fruit (LN16011) and *Sphaeranthus indicus* flower head (LN16015).

Intracellular ATP level was measured by luminescence based ATP detection assay system, ATPlite (PerkinElmer Inc., Waltham, Mass.). Briefly, L6 rat skeletal muscle cells were grown in a 96 well plate in RPMI, supplemented with 10% FBS and 50 μg/ml of penicillin-streptomycin at 37° C. with 5% CO2. After 16 h, media was replaced with fresh media containing independently different concentrations of test samples LN16002, LN16005, LN16008, LN16011, 16012, LN16014 and LN16015, and incubated for 4 hours. The vehicle control cultures received only 0.2% DMSO (V/V). Finally, 50 μl of substrate solution was added to each well and incubated at room temperature for 5 min on a plate shaker. After 10 minutes of dark adaptation, the luminescence was read in a luminometer (Modulus Multimode Reader, Turner Biosystems Inc., Sunnyvale, Calif.). A serial dilution of an ATP standard solution ranging from $1 \times 10^{-5}$ M to blank was applied to the assay plate. Intracellular ATP level was quantitatively estimated from a standard curve plotted with luminescence units vs. known concentrations of ATP. The cellular ATP index in the treated cultures was calculated by comparing the ATP content in the treated samples with the ATP content in the vehicle control cultures. The ATP content in the vehicle control cultures was considered as 100 percent. All the treatment concentrations for each sample were treated in quadruplicate wells. The hydroalcohol extracts of *Bauhinia racemosa* fruit (LN16002), *Mangifera indica* stem bark (LN16005), *Woodfordia fruticosa* tender stem (LN16008) and *Acacia nilotica* fruit (LN16011) potently increased the intracellular ATP concentration. The intracellular ATP index (%) data is summarized in Table 5. Similarly, *Mangifera indica* stem bark 80% methanol extract (LN16014) showed 29.2%, 38.7% and 44.3% increase in ATP concentration at doses of 5, 25 and 125 ng/mL respectively over that shown by untreated control cells. The ATP data obtained for extracts derived from other plant parts and those derived using other solvent media for extraction are also summarized in table-5 respectively.

TABLE 5

| Sample ID | Treatment conc. | ATP Content (%) |
|---|---|---|
| Vehicle control | 0.2% DMSO | 100 |
| LN16002 | 1 ng/ml | 117.08 |
| | 5 ng/ml | 128.76 |
| | 25 ng/ml | 125.97 |
| | 125 ng/ml | 130.86 |
| LN16005 | 1 ng/ml | 137.43 |
| | 5 ng/ml | 130.38 |
| | 25 ng/ml | 143.05 |
| | 125 ng/ml | 144.05 |
| Control | DMSO 0.2% (v/v) | 100 |
| LN16008 | 10 ng/ml | 130.6 |
| | 50 ng/ml | 136.52 |
| | 250 ng/ml | 149.75 |
| LN16011 | 10 ng/ml | 136.17 |
| | 50 ng/ml | 136.16 |
| | 250 ng/ml | 130.29 |
| LN17090 | 1 ng/ml | 107.06 |
| | 5 ng/ml | 116.24 |
| | 25 ng/ml | 118.30 |
| LN17095 | 10 ng/ml | 105.76 |
| LN17098 | 10 ng/ml | 103.98 |
| LN17093 | 10 ng/ml | 131.76 |
| LN17104 | 10 ng/ml | 125.82 |
| LN17105 | 10 ng/ml | 109.43 |
| LN16010 | 10 ng/ml | 120.04 |
| LN16011 | 10 ng/ml | 116.87 |
| LN16012 | 10 ng/ml | 108.94 |
| LN16001 | 10 ng/ml | 109.6 |
| LN17106 | 10 ng/ml | 105.78 |

Example 12

Evaluation of the ATP enhancing efficacy of the Compositions-1 to 5 and Compositions-11 to 32: The efficacy of the novel compositions Compositions-1 to 5 and Compositions-11 to 32 to increase the ATP levels in L6 rat skeletal muscle cells was evaluated using the test procedure disclosed above for Example 11. The data is summarized in tables 6 to 11

TABLE 6

| | ATP Assay (10 ng/ml) | | | | | | |
|---|---|---|---|---|---|---|---|
| | LN16005 | | LN16015 | | | % increase | % increase |
| | | % | | % | | Additive | Observed |
| Test sample | ng/mL | increase | ng/mL | increase | Ratio | (calculated) | at 1 ng/ml |
| Composition-2 | 2.5 | 3.52 | 7.5 | 6.28 | 1:3 | 9.78 | 22.2 |
| Composition-4 | 5.0 | 4.12 | 5.0 | 1.81 | 1:1 | 5.93 | 7.35 |
| Composition-5 | 6.66 | 5.49 | 3.33 | 1.20 | 2:1 | 6.69 | 17.46 |

TABLE 7

ATP assay (1 ng/ml)

| Test sample | LN16005 ng/mL | % increase | LN16011 ng/mL | % increase | Ratio | % increase Additive (calculated) | % increase Observed at 1 ng/ml |
|---|---|---|---|---|---|---|---|
| Composition-11 | 0.34 | 1.82 | 0.66 | 4.09 | 1:2 | 5.91 | 13.4 |
| Composition-12 | 0.50 | 2.68 | 0.50 | 3.1 | 1:1 | 5.78 | 18.25 |
| Composition-13 | 0.66 | 3.54 | 0.34 | 2.1 | 2:1 | 5.64 | 16.32 |

TABLE 8

ATP assay (5 ng/ml)

| Test sample | LN16011 ng/mL | % increase | LN17091 ng/mL | % increase | Ratio | % increase Additive (calculated) | % increase Observed at 5 ng/ml |
|---|---|---|---|---|---|---|---|
| Composition-14 | 1.6 | 1.25 | 3.4 | 5.76 | 1:2 | 7.01 | 12.30 |
| Composition-15 | 2.5 | 1.95 | 2.5 | 4.24 | 1:1 | 6.19 | 13.91 |
| Composition-16 | 3.4 | 2.65 | 1.6 | 2.71 | 2:1 | 5.36 | 10.54 |

TABLE 9

ATP Assay (5 ng/ml)

| Test sample | LN16005 ng/mL | % increase | LN17090 ng/mL | % increase | Ratio | % increase Additive (calculated) | % increase Observed at 5 ng/ml |
|---|---|---|---|---|---|---|---|
| Composition-17 | 1.6 | 3.41 | 3.4 | 11.22 | 1:2 | 14.63 | 20.63 |
| Composition-18 | 2.5 | 5.34 | 2.5 | 8.25 | 1:1 | 13.59 | 18.85 |
| Composition-19 | 3.4 | 7.26 | 1.6 | 5.28 | 2:1 | 12.54 | 16.32 |

TABLE 10

ATP Assay (25 ng/ml)

| Test sample | LN17091 ng/mL | % increase | LN17090 ng/mL | % increase | Ratio | % increase Additive (calculated) | % increase Observed at 25 ng/ml |
|---|---|---|---|---|---|---|---|
| Composition-20 | 16.66 | 0.03 | 8.34 | 0.38 | 2:1 | 0.41 | 13.05 |
| Composition-21 | 12.5 | 0.03 | 12.5 | 0.57 | 1:1 | 0.6 | 8.84 |
| Composition-22 | 8.34 | 0.02 | 16.66 | 0.75 | 1:2 | 0.77 | 17.5 |

TABLE 11

ATP Assay (1 ng/ml)

| Test sample | LN17090 ng/mL | LN17090 % increase | LN16011 ng/mL | LN16011 % increase | Ratio | % increase Additive (calculated) | % increase Observed at 1 ng/ml |
|---|---|---|---|---|---|---|---|
| Composition-25 | 0.66 | 0.54 | 0.34 | 00 | 2:1 | 0.54 | 5.19 |
| Composition-23 | 0.34 | 0.28 | 0.66 | 00 | 1:2 | 0.28 | 3.4 |

Example 13

Immunoblot Assay: Evaluation of the efficacy of the hydroalcohol extracts of *Bauhinia racemosa* fruit (LN16002), *Mangifera indica* stem bark (LN16005), *Woodfordia fruticosa* tender stem(LN16008) and *Acacia nilotica* fruit (LN16011), alcohol extract of *Cassia auriculata* leaves (LN17090) and composition-3 in modulating muscle markers proteins Phospho mTOR (Ser2448), m-TOR, PGC-1α, Myogenin and MyoD. The effects of the test samples on the muscle specific marker proteins in L6 rat skeletal muscle cells were analyzed using immunoblot assay. Briefly, L6 cells were treated with the test samples (LN16002, LN16005, LN16008 and LN16011) for different time period as indicated. Thereafter, the cells were washed three times with chilled PBS the cell lysates were prepared in a lysis buffer (10 mM Tris-HCl, pH 7.4, 150 mM NaCl, 1 mM EDTA, 1% Triton X-100) containing a protease inhibitor cocktail. The cell lysates were clarified at 14,000 g for 20 min at 4° C. The protein concentrations were estimated by Bradford reagent.

Equal amount of proteins was resolved in SDS-PAGE. Following SDS-PAGE, the electro-blotted nitrocellulose membranes were reacted overnight at 4° C. with various antibodies (specific to PhosphomTOR (Ser2448), m-TOR, PGC-1α, Myogenin, MyoD). The same membrane was re-incubated with anti-GAPDH antibody. Specific signals were detected with enhanced chemiluminescence (Thermo scientific, USA) and the signal intensities were captured by Gel Doc™ XR+ Imaging System and analyzed using Image Lab™ 2.0 Software (BioRad, Hercules, Calif.). The test compounds LN16002, LN16005, LN16008, LN16011, LN17090 and composition-3 potently ameliorated the muscle specific marker proteins PhosphomTOR (Ser2448), m-TOR, PGC-1α, Myogenin, MyoD, Myf6 as summarized in FIGS. 1A to 1F.

Example 14

Mitochondrial Biogenesis Assay: Evaluation of Mitochondrial biogenesis enhancing potential of hydroalcohol extracts of *Bauhinia racemosa* fruit (LN16002), *Woodfordia fruticosa* tender stem (LN16008), *Acacia nilotica* fruit (LN16011), alcohol extract of *Cassia auriculata* leaves (LN17090), composition-3 and compositions 26-31. The mitochondrial biogenesis was measured using MitoBiogenesis™ In-Cell ELISA Kit (Abcam, Cambridge, UK). This assay is based on measurement of ratios between 'subunit I of Complex IV' (COX-I), a mitochondrial DNA (mtDNA) encoded protein and 'Succinate dehydrogenase complex-subunit A' (SDH-A), a nuclear DNA (nDNA) encoded protein. Briefly, equal number of L6 rat skeletal myoblasts was seeded in each well of a poly L-lysine coated 96-well plate and incubated overnight at 37° C. in a CO2 incubator. The cells were treated with either LN16002 or LN16008 or LN16011 at different concentration for three consecutive days. The vehicle cultures wells receiving 0.2% DMSO were considered as the vehicle control. The cells were fixed with 4% paraformaldehyde for 20 min at room temperature. Then the washed cells were incubated with 0.5% acetic acid for 5 min to block endogenous alkaline phosphatase activity. Thereafter, the cells were permeabilized with permeabilization buffer and incubated further with primary antibody solution overnight at 4° C. The washed cells were further incubated with AP/HRP labeled Secondary Antibody Solution. Finally, the alkaline phosphatase and horse radish peroxidase reactions were developed for detection of SDH-A and COX-1, respectively as per protocol. Color reactions developed for SDH-A and COX-1 were read at 405 and 600 nm, respectively in a microplate reader (Spectra MaxM5, Molecular devices, Sunnyvale, Calif.). The percentage increase in mitochondrial biogenesis, when compared to control, was calculated and the data is summarized in Table 12,13 &13A below. The modulation of Cytochrome C oxidase 1 (COX1) by hydroalcohol extracts of *Bauhinia racemosa* fruit (LN16002), *Woodfordia fruticosa* tender stem (LN16008), *Acacia nilotica* fruit (LN16011), alcohol extract of *Cassia auriculata* leaves (LN17090) and composition-3 is summarized FIGS. 2A to 2F.

TABLE 12

| Sample ID | Treatment Conc. | % increase of mitochondrial biogenesis over vehicle control |
|---|---|---|
| LNE16002 | 25 ng/ml | 62.07 |
| LN16008 | 25 ng/ml | 49.71 |
| LN16011 | 25 ng/ml | 80.46 |
| LN16005 | 25 ng/mL | 35.64 |
| LN17090 | 25 ng/mL | 25.75 |
| Composition-3 | 25 ng/mL | 43.61 |

TABLE 13

% increase of mitochondrial biogenesis over vehicle control

| Test sample | LN17092 ng/mL | LN17092 % increase | LN16048 ng/mL | LN16048 % increase | Ratio | % increase Additive (calculated) | % increase Observed at 1 ng/ml |
|---|---|---|---|---|---|---|---|
| Composition-30 | 0.75 | 3.77 | 025.99 | 1.06 | 3:1 | 4.83 | 10.5 |

TABLE 13-continued

% increase of mitochondrial biogenesis over vehicle control

| Test sample | LN17092 | | LN16048 | | | % increase | % increase |
| | ng/mL | % increase | ng/mL | % increase | Ratio | Additive (calculated) | Observed at 1 ng/ml |
| --- | --- | --- | --- | --- | --- | --- | --- |
| Composition-31 | 0.66 | 3.31 | 0.33 | 1.40 | 2:1 | 4.71 | 10.03 |

TABLE 13A

% increase of mitochondrial biogenesis over vehicle control

| Test sample | LN17090 | | LN16048 | | | % increase | % increase |
| | ng/mL | % increase | ng/mL | % increase | Ratio | Additive (calculated) | Observed at 1 ng/ml |
| --- | --- | --- | --- | --- | --- | --- | --- |
| Composition-26 | 0.66 | 3.43 | 0.33 | 1.40 | 2:1 | 4.83 | 8.13 |
| Composition-27 | 0.5 | 2.6 | 0.5 | 2.13 | 1:1 | 4.73 | 7.65 |
| Composition-28 | 0.33 | 1.71 | 0.66 | 2.81 | 1:2 | 4.52 | 8.47 |
| Composition-29 | 0.25 | 1.30 | 0.75 | 3.19 | 1:3 | 4.49 | 7.37 |

Example 15

Myotube Assay: Evaluation of myotube (muscle fiber) forming efficacy of the hydroalcohol extracts of *Bauhinia racemosa* fruit (LN16002), *Woodfordia fruticosa* tender stem (LN16008) *Acacia nilotica* fruit (LN16011) and *Cassia auriculata* leaves (LN17090) and composition-3. Equal number of C2C12 mouse myoblast cells was seeded in a 24-well cell culture plate and incubated at 37° C. in a $CO_2$ incubator overnight. Next day, the cells were treated with multiple concentrations of test samples LN16002, LN16005, LN16008, LN16011 and 16012 (prepared in DMEM supplemented with 10% FBS). The vehicle control culture wells received cell culture medium containing only 0.1% DMSO. The cell culture medium along with the treatments was renewed at every 48 h and the plate was monitored every day for optimal differentiation. After four days of treatment, myotubes were formed and the culture was terminated. Thereafter, the cells were fixed with 2% Para formaldehyde and the formed myotubes were observed under 20× magnification at bright field and the phase contrast images were captured under a microscope (Axio observer Z1, Carl Zeiss). The cells treated with hydroalcohol extracts of *Bauhinia racemosa* fruit (LN16002), *Woodfordia fruticosa* tender stem (LN16008) *Acacia nilotica* fruit (LN16011), and *Cassia auriculata* leaves (LN17090) and composition-3 showed dose dependent improvement in the myotube formation when compared to the cells treated with control. The data is depicted in FIGS. 3A to 3E.

Example 16

Evaluation 20S Proteasome inhibition activity of the alcohol extract of *Cassia auriculata* leaves (LN17090) and composition-3 in L6 rat skeletal myoblasts: Proteasome activity assay was performed by using Cayman's 20S Proteasome assay kit (Ann Arbor, Mich., Cat #10008041) according to the manufacturer's protocol. It employs a specific 20S substrate, SUC-LLVY-AMC which, upon cleavage by the active enzyme, generates a highly fluorescent product with an emission wavelength at 480 nm. For the assay, approximately $1 \times 10^5$ to $1 \times 10^6$ L6 cells (ATCC, Manassas, Va.; Cat #CRL-1458) were seeded in a T-75 flask and incubated at 37° C. in a $CO_2$ incubator. After two days, cells were washed with 1XPBS, three times and 3 mL of assay buffer was added to the flask. Assay buffer was removed and 2 mL of lysis buffer was added (provided by the kit). The cells were scrapped, and the resulting lysate contained protein. Protein content in the lysate was estimated using Pierce BCA protein assay kit (Thermo Scientific, Waltham, Mass.; Cat #23225). Ten microliters of sample at desired concentration and approximately 0.4 mg/mL protein were added to each well. Ten microliters of substrate was added and incubated at 37° C. for one hour. After the incubation period, fluorescence intensity of each well was measured with Ex: 360 nm/Em: 480 nm in a Spectramax 5e multi-mode reader (Molecular Devices, Sunnyvale, Calif.). The intensity of the test compound was compared with that of the control well to obtain the percentage inhibition of the 20S proteasome activity. The data for LN17090 and Composition-3 is summarized in FIGS. 2A to 2F.

Example 17

Efficacy of LN17090 and Composition-3 to recover from depolarized mitochondrial membrane potential in H2O2 induced L6 rat skeletal myoblasts, Mitochondrial membrane potential assay: Mitochondrial membrane potential ($\Delta\psi_M$) was measured using a cytofluorimetric, lipophilic cationic dye, 5,5',6,6'-Tetrachloro-1,1',3,3'-tetraethylbenzimidazolyl-carbo-cyanine iodide (JC-1, Thermofisher Scientific; Cat #T3168). Briefly, L-6 (ATCC, Manassaas, Va; Cat #CRL-1458) rat skeletal myoblasts were harvested from the culture flasks and $0.1 \times 10^6$ cells/mL in 1XPBS were taken in FACS tubes. Samples at required concentrations were prepared in 1XPBS, added to respective tubes and incubated for 30 minutes at 37° C. in a $CO_2$ incubator. $H_2O_2$ (5 mM final concentration) was added to all the tubes except for control and JC-1 tubes and incubated them for 15 minutes at 37° C. in a $CO_2$ incubator. JC-1 (0.5 μg/mL) was added to all the tubes except control tube and incubated for 30 minutes at 37° C. in a $CO_2$ incubator. All the tubes were centrifuged at 1300 rpm for five minutes. Supernatant was discarded and cells were resuspended in 1 mL of warm 1XPBS, centrifuged at 1300 rpm for 5 minutes. Cells were resuspended in 2004 of 1XPBS and acquired in a BD FACSVerse flow cytometer and analyzed by FACS Suite software to obtain the percentage of depolarized cells for the control, $H_2O_2$ treated cell and cells treated with test compounds. The data is summarized in Table 14.

TABLE 14

| Samples | Treatment Conc. | % cell population recovered from depolarization |
|---|---|---|
| LN16005 | 5 ng/mL | 58.15 |
| LN16008 | 5 ng/mL | 53.19 |
| LN16011 | 100 ng/mL | 15.62 |
|  | 125 ng/mL | 20.62 |
| LN17090 | 5 ng/ml | 5.90 |
|  | 25 ng/mL | 44.89 |
| Composition-3 | 50 ng/mL | 47.08 |

Example 18

Evaluation of energy, endurance and muscle strength enhancing potential of hydroalcohol extract of *Acacia nilotica* fruit (LN16011) and a composition-1 containing 80% methanol extract of *Mangifera indica* bark (LN16014) and *Sphaeranthus indicus* (LN16015) extract and excipients. Swiss albino mice were acclimatized for 5 days before initiation of the study. Healthy Swiss albino mice were selected and randomly divided (n=6) into different treatment groups. The groups G1 to G3 of Swiss albino mice were administered orally with vehicle, composition-1 (150 mg/kg) and LN16011 (200 mg/kg) respectively, for 21 days to evaluate the energy endurance and muscle strength potential of these compounds.

On day 21, one hour after the treatment the mice were forced to swim with a constant load (10% of its body weight attached to its tail) in an acrylic cylinder filled with water. This test was monitored for 10 minutes using the SMART video tracking system (Panlab S.L.U). Various swimming parameters were recorded and analyzed by smart software. The measured swimming parameters include, resting time, slow moving time, fast moving time, total moving time, path length of swimming and average velocity. The results were expressed as mean±SEM and compared with control group to measure efficacy and the results are summarized in Table 15.

TABLE 15

| Parameters | G1-FST + Vehicle control | G2-FST + composition-1 (150 mg/kg) | G3-FST + LN16011 (200 mg/kg) |
|---|---|---|---|
| Distance Travelled (cm) | 37823.03 ± 4414.18 | 48574.63 ± 5471.68 | 47155.87 ± 2067.30 |
| Resting Time (sec) | 126.93 ± 23.84 | 123.53 ± 49.90 | 102.48 ± 8.06 |
| Slow Swimming Time (sec) | 308.8 ± 19.16 | 298.27 ± 28.91 | 331.84 ± 7.47 |
| Fast Swimming Time (sec) | 112.33 ± 19.81 | 178.1 ± 28.60 | 165.68 ± 16.13 |
| Total (Fast + Slow) Swimming Time (sec) | 421.13 ± 37.67 | 476.37 ± 49.89 | 497.52 ± 9.06 |
| Average Velocity (cm/sec) | 68.39 ± 5.87 | 80.97 ± 9.12 | 78.59 ± 3.45 |

Values are expressed as Mean ± SEM;
n = 6 animals/group

The animal groups supplemented with the test items Composition-1 and LN16011 showed a reduction in resting time (sec) and increase in distance travelled (mm), slow swimming time (sec), fast swimming time (sec) on day 21 of the study. The above observations indicate that the animals treated with composition-1 and LN16011 were more active and energetic during 10 minutes of forced swimming period and could tend to swim either slow or fast most of the time rather than resting as compared to control group. The increase in percent fast swimming and swimming velocity in group on day 21 reveals that the treated animals tend to swim fast and covered longer distances in the shortest period of time after oral administration of composition-1 and LN16011 as compared to control group. Hence, the animals treated with these compositions composition-1 and extract LN16011 are more energetic. In addition, an improved energy, the increase in distance travelled and reduced resting time indicate that the composition composition-1 and extract LN16011 have higher endurance over the control.

After 21 days of treatment Grip strength of mice was measured by using Grip strength meter (UgoBasile, Italy). Animals were trained and habituated to the experimental environment and conditions for 5 days before grip strength measurement. Each mouse was allowed to grasp the grasping bar and it was pulled back gently in a horizontal plane by tail with gradually increasing force till the pulling force overcomes the grip strength of the animal. The force applied at the moment when the mice leave its grasp on the grasping bar was recorded as grip strength in grams. Three trials were conducted on each animal and average grip strength was calculated. The results were expressed as mean±SEM and compared with control group and were summarized in Table 16.

TABLE 16

| Group | Average Grip Strength measured after 21 Days |
|---|---|
| FST control | 66.61 ± 8.40 |
| Composition-1 | 94.33 ± 2.38 |
| LN16011 | 104.20 ± 5.63 |

Values are expressed as Mean ± SEM;
n = 6 animals/group

Based on the data, it is obvious that animals in the groups treated with composition-1 and LN16011 for 21 days exhibited relatively better grip strength when compared control. Hence, it can be concluded that these compounds increase the muscle strength.

Example 19

Efficacy of Composition-33, Composition-34, Composition-35, Composition-36, and Composition-37 for Muscle Strength and Energy Endurance Potential in Swiss albino Mice: The animals were acclimatized for a period of 3 days prior to enrollment into the study. A group of 60 Swiss albino male mice of age group 7-9 weeks and body weight 23.0-42.0 g were examined, and 54 healthy mice were selected for experiment and were randomly assigned to nine groups. Each group comprised of 6 animals each with vehicle control, test items and positive control L-carnitine. Test items Compositions-33-37 were administered orally at 200 mpk. L-carnitine was administered orally at 150 mpk for a period of 21 days. On day 21 animals were evaluated for grip strength and forced swimming test. Grip strength was performed by allowing the mice to hold the bar with fore limb; gently pulling the mice by tail the grip strength in lbs was recorded in triplicates for all individual animals. Forced Swim was briefly performed in acrylic tank filled up to 27 cm were the mice was forced to swim with the weight of 5% body weight burdened to the tail of mouse. Initially grip strength after 1 hour of test items administrations were done; followed by forced swim test for 10 min. In forced swim test the animals swimming parameters such as slow swimming, resting, fast swimming and total distance (length) covered was recorded using SMART video tracking software. Immediately after 10 minutes of stipulated time of swimming the animals were sacrificed using over dose of $CO_2$, gastrocnemius muscle was snap frozen to analyze biomarker mTOR.

TABLE 17

Summary of Swimming Parameters on Day 21

| Parameters | G1-FST + Vehicle control | G2-FST + Composition-33 | G4-FST + Composition-34 | G5-FST + Composition-35 |
|---|---|---|---|---|
| Resting Time (sec) | 427.36 ± 29.05 | 382.07 ± 33.04 | 339.08 ± 76.22 | 375.07 ± 76.93 |
| Slow Swimming Time (sec) | 125.80 ± 22.97 | 140.50 ± 17.22 | 165.24 ± 46.75 | 141.83 ± 48.10 |
| Fast Swimming Time (sec) | 46.84 ± 7.44 | 77.27 ± 20.09 | 95.68 ± 30.05 | 80.97 ± 30.65 |
| Total (Fast + Slow) Swimming Time (sec) | 172.64 ± 29.05 | 217.77 ± 32.94 | 260.92 ± 76.22 | 222.80 ± 78.40 |
| Distance Travelled (cm) | 16239.35 ± 2155.68 | 20703.14 ± 3176.59 | 23518.76 ± 5985.02 | 20253.77 ± 6349.12 |

| Parameters | G6-FST + Composition-36 | G8-FST + Composition-37 | G9-FST + L-Carnitine |
|---|---|---|---|
| Resting Time (sec) | 350.48 ± 42.21 | 341.63 ± 38.93 | 407.80 ± 25.98 |
| Slow Swimming Time (sec) | 187.24 ± 38.44 | 181.07 ± 29.41 | 140.50 ± 23.01 |
| Fast Swimming Time (sec) | 62.28 ± 12.58 | 77.30 ± 10.73 | 51.70 ± 9.49 |
| Total (Fast + Slow) Swimming Time (sec) | 249.52 ± 42.21 | 258.37 ± 38.93 | 192.20 ± 25.98 |
| Distance Travelled (cm) | 20663.27 ± 2883.56 | 23124.52 ± 2743.52 | 19224.72 ± 1998.85 |

Values are expressed as Mean ± S.E.M, n = 6 animals/group

TABLE 18

Summary of Grip Strength (lbs)

| Group | Day 21 |
|---|---|
| G1-FST + Vehicle control | 0.21 ± 0.01 |
| G2-FST + Composition-33 | 0.28 ± 0.01 |
| G4-FST + Composition-34 | 0.28 ± 0.02 |
| G5-FST + Composition-35 | 0.21 ± 0.02 |
| G6-FST + Composition-36 | 0.30 ± 0.02 |
| G8-FST + Composition-37 | 0.27 ± 0.01 |
| G9-FST + L-Carnitine Hydrochloride | 0.32 ± 0.01 |

Values are expressed as Mean ± S.E.M;
n = 6 animals/group

Example 20

Efficacy of LN16011 and LN17090 in improving Grip strength, Muscle endurance, and Muscle fiber diameter size in Dexamethasone induced Sarcopenia model of Sprague Dawly (SD) rats: The animals were acclimatized for a period of 3 days prior to enrollment into the study. A group of 40 rats of age group 6 to12 weeks and body weight 170 to 320 g were examined and 36 healthy rats were selected for experiment and they were randomly assigned to 6 groups. All the groups comprised of 6 animals each with vehicle control (G1), dexamethasone induced disease control (G2), 200 mg/kg LN17090 supplemented group (G3), 400 mg/kg LN17090 supplemented group (G4), 200 mg/kg LN16011 supplemented group (G5) and 350 mg/kg HMB (beta-hydroxy beta-methyl butyrate) supplemented positive control group (G6). The supplementation of test items and standard were initiated on day 1 and continued throughout the study until day 21. Sarcopenia was induced in animals by dosing the animals with dexamethasone at 4 mpk from day 8 to day 14. On day 21, animals were evaluated for Grip strength, Muscle endurance, muscle fibre diameter in gastrocnemius and soleus muscle tissue. Grip strength was performed by allowing the mice to hold the bar with fore limb; gently pulling the mice by tail and the grip strength in lbs was recorded in triplicates for all individual animals. Muscle endurance was evaluated by hanging the animal upside down from a steel grill and falling time in seconds was recorded as endurance. At the end of the study the animals were euthanized and soleus and gastrocnemius muscles were submitted for Histomorphometry. The muscle tissues were processed, sectioned, stained, examined under microscope and muscle fiber diameter was measured in randomly selected fibers. The data for all the parameters is summarized in FIGS. 4A to 4D.

We claim:

1. A herbal composition comprising a synergistic mixture of at least two ingredients, wherein the synergistic mixture comprises:
a first mixture comprising an extract of *Mangifera indica* and a second component in a ratio of from 4:1 to 1:4, said second component being an extract of a plant selected from the group consisting of *Acacia nilotica, Cassia auriculata, Sphaeranthus indicus*, and mixtures thereof; or
a second mixture comprising an extract of *Cassia auriculata* and a fourth component in a ratio of from 4:1 to 1:4, said fourth component being an extract of a plant selected from the group consisting of *Acacia nilotica, Punica granatum, Rubia cordifolia*, and mixtures thereof; or
a mixture thereof;
said synergistic mixture being present in an amount effective to treat a subject in need thereof by:
providing increased energy or improved maintenance of energy to the subject;
providing improved mental alertness to the subject;
providing increased muscle strength or muscle mass to the subject; or
treating sarcopenia or muscular atrophy in the subject.

2. The herbal composition of claim 1, further comprising at least one compound selected from the group consisting of biological actives, herbal extracts, minerals, amino acids, proteins, vitamins, excipients, diluents, carriers, as a natural energy enhancer.

3. The herbal composition of claim 1, further comprising:
an extract of *Bauhinia racemosa, Woodfordia fruticose*, or a mixture thereof.

4. The herbal composition of claim 1, comprising:
the extract of *Mangifera indica* and the second component in a ratio of between 2:1 and 1:3, the second component being an extract of *Acacia nilotica, Cassia auriculata, Sphaeranthus indicus*, or a mixture thereof.

5. The herbal composition of claim 4, wherein the composition comprises:
the extract of *Mangifera indica* and the second component in a ratio of between 2:1 and 1:2, the second component comprising an extract of *Acacia nilotica*.

6. The herbal composition of claim 4, wherein the composition comprises:
the extract of *Mangifera indica* and the second component in a ratio of between 2:1 and 1:2, the second component comprising an extract of *Cassia auriculata*.

7. The herbal composition of claim 1, wherein the composition comprises:
the extract of *Cassia auriculata* and the fourth component in a ratio of between 3:1 and 1:3, the fourth component being an extract of a plant selected from the group consisting of *Acacia nilotica, Punica granatum, Rubia cordifolia*, and mixtures thereof.

8. A dietary supplement or herbal product, comprising the herbal composition of claim 1.

9. The herbal composition of claim 1, wherein:
the extracts of *Acacia nilotica, Bauhinia racemosa, Cassia auriculata, Mangifera Woodfordia fruticosa, Sphaeranthus indicus, Punica granatum*, and *Rubia cordifolia* are each prepared by extraction of a plant part with a solvent selected from the group consisting of C1-C5 alcohols; water; C1-C7 hydrocarbons; ethyl acetate; MIBK; acetone; and mixtures thereof.

10. The herbal composition of claim 1, wherein:
the extracts of *Acacia nilotica, Bauhinia racemosa, Cassia auriculata, Mangifera Woodfordia fruticosa, Sphaeranthus indicus, Punica granatum*, and *Rubia cordifolia* are each prepared by extraction of a plant part,
the plant part being selected from the group consisting of leaves, stems, tender stem, aerial parts, fruit, fruit rind, seed, flower heads, root, bark, whole plant, and mixtures thereof.

11. The herbal composition of claim 1, wherein:
said herbal composition is formulated into a dosage form, said dosage form being:
a dry powder, a liquid, a food product, a beverage, a tablet, a capsule, a chewable tablet, a soft gel capsule, a controlled release tablet, a polymer coated tablet, microcapsules, or a colloid.

12. The herbal composition of claim 1, further comprising an excipient, carrier, or diluent, said excipient, carrier, or diluent being selected from the group consisting of glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, proteins, calcium salts, pigments, flavors, preservatives, distilled water, saline, aqueous glucose solution, alcohol, propylene glycol and polyethylene glycol, various animal and vegetable oils, white soft paraffin, paraffin, flavorants, colorants, a wax, and mixtures thereof.

13. A herbal composition comprising a synergistic mixture of at least two ingredients, wherein the synergistic mixture comprises:
   an extract of *Mangifera indica* and a second component in a ratio of between 2:1 and 1:3, the second component comprising being an extract of *Sphaeranthus indicus;*
   said synergistic mixture being present in an amount effective to treat a subject in need thereof by:
   providing increased energy or improved maintenance of energy to the subject;
   providing improved mental alertness to the subject;
   providing increased muscle strength or muscle mass to the subject; or
   treating sarcopenia or muscular atrophy in the subject.

14. A dietary supplement or herbal product, comprising the herbal composition of claim 13.

15. A method of increasing endurance, muscle mass, and/or muscle strength in a mammal,
   wherein the method comprises administering to the mammal a therapeutically effective amount of the herbal composition of claim 1.

16. A method of increasing endurance, muscle mass, and/or muscle strength in a mammal,
   wherein the method comprises administering to the mammal a therapeutically effective amount of the herbal composition of claim 13.

17. A method of treating sarcopenia or muscular atrophy in a mammal,
   wherein the method comprises administering to the mammal a therapeutically effective amount of the herbal composition of claim 1.

18. A method of treating sarcopenia or muscular atrophy in a mammal,
   wherein the method comprises administering to the mammal a therapeutically effective amount of the herbal composition of claim 13.

19. A method of increasing muscle mass or muscle strength in a mammal in need thereof,
   wherein the method comprises administering to the mammal a therapeutically effective amount of a dietary supplement or herbal product comprising the herbal composition of claim 1,
   in combination with:
   at least one ingredient selected from the group consisting of excipients, carriers, diluents, sweeteners, flavorants, colorants, vitamins, proteins, and amino acids.

20. The method of claim 19, wherein the mammal suffers from sarcopenia or muscular atrophy.

* * * * *